(12) United States Patent
Auwerx et al.

(10) Patent No.: US 9,180,134 B2
(45) Date of Patent: Nov. 10, 2015

(54) MITOCHONDRIAL RIBOSOMAL PROTEINS AS AGING REGULATORS

(75) Inventors: Johan Auwerx, Buchillon (CH); Richardus Houtkooper, Amsterdam (NL); Laurent Mouchiroud, Morges (CH)

(73) Assignee: ECOLE POLYTECHNIQUE FEDERALE DE LAUSANNE (EPEL), Lausanne (CH)

( * ) Notice: Subject to any disclaimer, the term of this patent is extended or adjusted under 35 U.S.C. 154(b) by 0 days.

(21) Appl. No.: 14/239,198

(22) PCT Filed: Aug. 20, 2012

(86) PCT No.: PCT/IB2012/054206
§ 371 (c)(1),
(2), (4) Date: Feb. 17, 2014

(87) PCT Pub. No.: WO2013/024467
PCT Pub. Date: Feb. 21, 2013

(65) Prior Publication Data
US 2014/0187611 A1 Jul. 3, 2014

Related U.S. Application Data

(60) Provisional application No. 61/524,889, filed on Aug. 18, 2011.

(51) Int. Cl.
| | |
|---|---|
| *A61K 48/00* | (2006.01) |
| *A61K 31/65* | (2006.01) |
| *A61K 31/713* | (2006.01) |
| *C12N 15/113* | (2010.01) |
| *G01N 33/50* | (2006.01) |
| *A61K 31/165* | (2006.01) |
| *A61K 49/00* | (2006.01) |
| *C12Q 1/68* | (2006.01) |

(52) U.S. Cl.
CPC .............. *A61K 31/65* (2013.01); *A61K 31/165* (2013.01); *A61K 31/713* (2013.01); *A61K 49/0008* (2013.01); *C12N 15/113* (2013.01); *C12Q 1/6897* (2013.01); *G01N 33/5023* (2013.01); *G01N 33/5079* (2013.01); *G01N 33/5085* (2013.01); *C12N 2310/14* (2013.01)

(58) Field of Classification Search
None
See application file for complete search history.

(56) References Cited

U.S. PATENT DOCUMENTS

2003/0082120 A1   5/2003   Milstein

FOREIGN PATENT DOCUMENTS

| WO | WO 01/83524 | 11/2001 |
|---|---|---|
| WO | WO 03/087768 | 10/2003 |

OTHER PUBLICATIONS

Auwerx, J. et al. "Protein homeostasis in the control of mitochondrial function and aging" *CIG Symposium 2012*, Jun. 14, 2012, pp. 1-39, see p. 10, XP002689993.
Houtkooper, R. et al. "The metabolic footprint of aging in mice" *Scientific Reports*, Oct. 1, 2011, pp. 1-11, vol. 1.
Harrison, D. E. et al. "Rapamycin fed late in life extends lifespan in genetically heterogeneous mice" *Nature*, Jul. 16, 2009, pp. 392-395, vol. 460, No. 7253.
Fujii, M. et al. "Mutation in a mitochondrial ribosomal protein causes increased sensitivity to oxygen with decreased longevity in the nematode *Caenorhabditis elegans*" *Genes to Cells*, Dec. 13, 2010, pp. 69-79, vol. 16, No. 1.
Lee, S. S. et al. "A systematic RNAi screen identifies a critical role for mitochondria in *C. elegans* longevity" *Nature Genetics*, Jan. 1, 2003, pp. 40-48, vol. 33, No. 1.
Mouchiroud, L. et al. "Life span extension by resveratrol, rapamycin, and metformin: The promise of dietary restriction mimetics for an healthy aging" *BioFactors*, Sep. 2010, pp. 377-382, vol. 36, No. 5.
Houtkooper, R. H. et al. "Metabolic Networks of Longevity" *Cell*, Jul. 9, 2010, pp. 9-14, vol. 142, No. 1.
Hamilton, B. et al. "A systematic RNAi screen for longevity gens in *C. elegans*" *Genes & Development*, Jul. 1, 2005, pp. 1544-1555, vol. 19, No. 13.
Heeren, G. et al. "The mitochondrial ribosomal protein of the large subunit, Afo1p, determines cellular longevity through mitochondrial back-signaling via TOR1" *Aging*, Jul. 2009, pp. 622-636, vol. 1, No. 7.
Suzuki, T. et al. "Proteomic Analysis of the Mammalian Mitochondrial Ribosome" *The Journal of Biological Chemistry*, Aug. 31, 2001, pp. 33181-33195, vol. 276, No. 35.
Kenyon, C. J. "The genetics of ageing" *Nature*, Mar. 25, 2010, pp. 504-512 and correction page, vol. 464.
Pearson, K. J. et al. "Resveratrol delays age-related deterioration and mimics transcriptional aspects of dietary restriction without extending lifespan" *Cell Metab.*, Aug. 2008, pp. 157-168, vol. 8, No. 2.
Written Opinion in International Application No. PCT/IB2012/054206, May 6, 2013, pp. 1-16.
Andreux, P. A. et al. "Pharmacological approaches to restore mitochondrial function" *Nat Rev Drug Discov.*, Jun. 2013, pp. 465-483, vol. 12, No. 6.
Reddy, P. H. et al. "Mitochondria as a Therapeutic Target for Aging and Neurodegenerative Disease" *Curr Alzheimer Res.*, Jun. 2011, pp. 393-409, vol. 8, No. 4.

*Primary Examiner* — Kimberly Chong
(74) *Attorney, Agent, or Firm* — Saliwanchik, Lloyd & Eisenschenk

(57) ABSTRACT

The present invention relates to methods of increasing lifespan, delaying aging, and/or preventing or treating an age-related disease or a mitochondrial disease in a subject, comprising inducing a nuclear-mitochondrial OXPHOS protein dyssynchrony, including inhibiting the mitochondrial translation machinery function, as well as methods for screening agents that are able to increase lifespan, inhibit or delay aging, and/or prevent or treat an age-related disease or disorder, or a mitochondrial disease or disorder, in a subject.

17 Claims, 8 Drawing Sheets

A

B

```
                          SEQUENCE LISTING

<160> NUMBER OF SEQ IDS: 10

<210> SEQ ID NO 1
<211> LENGTH: 430
<212> TYPE: PRT
<213> ORGANISM: Homo sapiens

<400> SEQUENCE: 1

Met Ala Thr Ala Val Arg Ala Val Gly Cys Leu Pro Val Leu Cys Ser
1               5                   10                  15

Gly Thr Ala Gly His Leu Leu Gly Arg Gln Cys Ser Leu Asn Thr Leu
            20                  25                  30

Pro Ala Ala Ser Ile Leu Ala Trp Lys Ser Val Leu Gly Asn Gly His
        35                  40                  45

Leu Ser Ser Leu Gly Thr Arg Asp Thr His Pro Tyr Ala Ser Leu Ser
    50                  55                  60

Arg Ala Leu Gln Thr Gln Cys Cys Ile Ser Ser Pro Ser His Leu Met
65                  70                  75                  80

Ser Gln Gln Tyr Arg Pro Tyr Ser Phe Phe Thr Lys Leu Thr Ala Asp
                85                  90                  95

Glu Leu Trp Lys Gly Ala Leu Ala Glu Thr Gly Ala Gly Ala Lys Lys
            100                 105                 110

Gly Arg Gly Lys Arg Thr Lys Lys Lys Arg Lys Asp Leu Asn Arg
            115                 120                 125

Gly Gln Ile Ile Gly Glu Gly Arg Tyr Gly Phe Leu Trp Pro Gly Leu
```

```
                130                 135                 140
Asn Val Pro Leu Met Lys Asn Gly Ala Val Gln Thr Ile Ala Gln Arg
145                 150                 155                 160

Ser Lys Glu Glu Gln Glu Lys Val Glu Ala Asp Met Ile Gln Gln Arg
                165                 170                 175

Glu Glu Trp Asp Arg Lys Lys Met Lys Val Lys Arg Glu Arg Gly
                180                 185                 190

Trp Ser Gly Asn Ser Trp Gly Gly Ile Ser Leu Gly Pro Pro Asp Pro
                195                 200                 205

Gly Pro Cys Gly Glu Thr Tyr Glu Asp Phe Asp Thr Arg Ile Leu Glu
                210                 215                 220

Val Arg Asn Val Phe Thr Met Thr Ala Lys Glu Gly Arg Lys Lys Ser
225                 230                 235                 240

Ile Arg Val Leu Val Ala Val Gly Asn Gly Lys Gly Ala Ala Gly Phe
                245                 250                 255

Ser Ile Gly Lys Ala Thr Asp Arg Met Asp Ala Phe Arg Lys Ala Lys
                260                 265                 270

Asn Arg Ala Val His His Leu His Tyr Ile Glu Arg Tyr Glu Asp His
                275                 280                 285

Thr Ile Phe His Asp Ile Ser Leu Arg Phe Lys Arg Thr His Ile Lys
                290                 295                 300

Met Lys Lys Gln Pro Lys Gly Tyr Gly Leu Arg Cys His Arg Ala Ile
305                 310                 315                 320

Ile Thr Ile Cys Arg Leu Ile Gly Ile Lys Asp Met Tyr Ala Lys Val
                325                 330                 335

Ser Gly Ser Ile Asn Met Leu Ser Leu Thr Gln Gly Leu Phe Arg Gly
                340                 345                 350

Leu Ser Arg Gln Glu Thr His Gln Gln Leu Ala Asp Lys Lys Gly Leu
                355                 360                 365

His Val Val Glu Ile Arg Glu Glu Cys Gly Pro Leu Pro Ile Val Val
                370                 375                 380

Ala Ser Pro Arg Gly Pro Leu Arg Lys Asp Pro Glu Pro Glu Asp Glu
385                 390                 395                 400

Val Pro Asp Val Lys Leu Asp Trp Glu Asp Val Lys Thr Ala Gln Gly
                405                 410                 415

Met Lys Arg Ser Val Trp Ser Asn Leu Lys Arg Ala Ala Thr
                420                 425                 430

<210> SEQ ID NO 2
<211> LENGTH: 325
<212> TYPE: PRT
<213> ORGANISM: Homo sapiens

<400> SEQUENCE: 2

Met Ala Ala Val Arg Cys Met Gly Arg Ala Leu Ile His His Gln
1               5                   10                  15

Arg His Ser Leu Ser Lys Met Val Tyr Gln Thr Ser Leu Cys Ser Cys
                20                  25                  30

Ser Val Asn Ile Arg Val Pro Asn Arg His Phe Ala Ala Ala Thr Lys
                35                  40                  45

Ser Ala Lys Lys Thr Lys Lys Gly Ala Lys Glu Lys Thr Pro Asp Glu
                50                  55                  60

Lys Lys Asp Glu Ile Glu Lys Ile Lys Ala Tyr Pro Tyr Met Glu Gly
65                  70                  75                  80
```

```
Glu Pro Glu Asp Asp Val Tyr Leu Lys Arg Leu Tyr Pro Arg Gln Ile
                85                  90                  95

Tyr Glu Val Glu Lys Ala Val His Leu Leu Lys Lys Phe Gln Ile Leu
            100                 105                 110

Asp Phe Thr Ser Pro Lys Gln Ser Val Tyr Leu Asp Leu Thr Leu Asp
        115                 120                 125

Met Ala Leu Gly Lys Lys Lys Asn Val Glu Pro Phe Thr Ser Val Leu
    130                 135                 140

Ser Leu Pro Tyr Pro Phe Ala Ser Glu Ile Asn Lys Val Ala Val Phe
145                 150                 155                 160

Thr Glu Asn Ala Ser Glu Val Lys Ile Ala Glu Glu Asn Gly Ala Ala
                165                 170                 175

Phe Ala Gly Gly Thr Ser Leu Ile Gln Lys Ile Trp Asp Asp Glu Ile
            180                 185                 190

Val Ala Asp Phe Tyr Val Ala Val Pro Glu Ile Met Pro Glu Leu Asn
        195                 200                 205

Arg Leu Arg Lys Lys Leu Asn Lys Lys Tyr Pro Lys Leu Ser Arg Asn
    210                 215                 220

Ser Ile Gly Arg Asp Ile Pro Lys Met Leu Glu Leu Phe Lys Asn Gly
225                 230                 235                 240

His Glu Ile Lys Val Asp Glu Arg Glu Asn Phe Leu Gln Thr Lys
                245                 250                 255

Ile Ala Thr Leu Asp Met Ser Ser Asp Gln Ile Ala Ala Asn Leu Gln
            260                 265                 270

Ala Val Ile Asn Glu Val Cys Arg His Arg Pro Leu Asn Leu Gly Pro
        275                 280                 285

Phe Val Val Arg Ala Phe Leu Arg Ser Ser Thr Ser Glu Gly Leu Leu
    290                 295                 300

Leu Lys Ile Asp Pro Leu Leu Pro Lys Glu Val Lys Asn Glu Glu Ser
305                 310                 315                 320

Glu Lys Glu Asp Ala
                325

<210> SEQ ID NO 3
<211> LENGTH: 305
<212> TYPE: PRT
<213> ORGANISM: Homo sapiens

<400> SEQUENCE: 3

Met Ala Leu Cys Ala Leu Thr Arg Ala Leu Arg Ser Leu Asn Leu Ala
1               5                   10                  15

Pro Pro Thr Val Ala Ala Pro Ala Pro Ser Leu Phe Pro Ala Ala Gln
            20                  25                  30

Met Met Asn Asn Gly Leu Leu Gln Gln Pro Ser Ala Leu Met Leu Leu
        35                  40                  45

Pro Cys Arg Pro Val Leu Thr Ser Val Ala Leu Asn Ala Asn Phe Val
    50                  55                  60

Ser Trp Lys Ser Arg Thr Lys Tyr Thr Ile Thr Pro Val Lys Met Arg
65                  70                  75                  80

Lys Ser Gly Gly Arg Asp His Thr Gly Arg Ile Arg Val His Gly Ile
                85                  90                  95

Gly Gly Gly His Lys Gln Arg Tyr Arg Met Ile Asp Phe Leu Arg Phe
            100                 105                 110

Arg Pro Glu Glu Thr Lys Ser Gly Pro Phe Glu Glu Lys Val Ile Gln
        115                 120                 125
```

```
Val Arg Tyr Asp Pro Cys Arg Ser Ala Asp Ile Ala Leu Val Ala Gly
            130                 135                 140

Gly Ser Arg Lys Arg Trp Ile Ile Ala Thr Glu Asn Met Gln Ala Gly
145                 150                 155                 160

Asp Thr Ile Leu Asn Ser Asn His Ile Gly Arg Met Ala Val Ala Ala
                165                 170                 175

Arg Glu Gly Asp Ala His Pro Leu Gly Ala Leu Pro Val Gly Thr Leu
            180                 185                 190

Ile Asn Asn Val Glu Ser Glu Pro Gly Arg Gly Ala Gln Tyr Ile Arg
            195                 200                 205

Ala Ala Gly Thr Cys Gly Val Leu Leu Arg Lys Val Asn Gly Thr Ala
        210                 215                 220

Ile Ile Gln Leu Pro Ser Lys Arg Gln Met Gln Val Leu Glu Thr Cys
225                 230                 235                 240

Val Ala Thr Val Gly Arg Val Ser Asn Val Asp His Asn Lys Arg Val
                245                 250                 255

Ile Gly Lys Ala Gly Arg Asn Arg Trp Leu Gly Lys Arg Pro Asn Ser
            260                 265                 270

Gly Arg Trp His Arg Lys Gly Trp Ala Gly Arg Lys Ile Arg Pro
            275                 280                 285

Leu Pro Pro Met Lys Ser Tyr Val Lys Leu Pro Ser Ala Ser Ala Gln
    290                 295                 300

Ser
305

<210> SEQ ID NO 4
<211> LENGTH: 432
<212> TYPE: PRT
<213> ORGANISM: Mus musculus

<400> SEQUENCE: 4

Met Ala Ala Ala Val Arg Ala Ala Gly Cys Leu Pro Ala Leu Cys Ser
1               5                   10                  15

Leu Gln Ala Gly His Phe Leu Ser Arg Gln Leu Ser Leu Asn Ala Phe
            20                  25                  30

Pro Val Ala Ala Thr Ser Phe Leu Ala Val Lys Thr Ala Leu Ser His
        35                  40                  45

Gly Ser Leu Ser Ser Arg Glu Thr Arg Arg Asn His Cys Leu Thr Ser
    50                  55                  60

Leu Ser His Val Leu Gln Thr Gln Cys Cys Val Ser Ser Pro Gly Asn
65                  70                  75                  80

Trp Thr Gly Gln Gln Cys Arg Pro Tyr Ser Phe Phe Thr Lys Leu Thr
                85                  90                  95

Ala Glu Glu Leu Trp Lys Gly Ala Leu Ala Glu Thr Gly Ala Gly Ala
            100                 105                 110

Arg Lys Gly Arg Gly Lys Arg Thr Lys Lys Lys Arg Lys Asp Leu
        115                 120                 125

Asn Arg Gly Gln Ile Ile Gly Glu Gly Arg Ser Gly Phe Leu Trp Pro
    130                 135                 140

Gly Leu Asn Val Pro Leu Ile Lys Ser Gly Val Val Gln Asn Ile Gly
145                 150                 155                 160

Gln Arg Ser Lys Glu Glu Gln Gln Lys Val Glu Ala Thr Met Val Glu
                165                 170                 175

Gln Arg Glu Glu Trp Asp Arg Lys Arg Lys Ile Lys Val Lys Arg Glu
```

```
                180                 185                 190
Arg Gly Trp Ser Gly Asn Thr Trp Gly Gly Val Ser Ile Gly Pro Pro
            195                 200                 205

Asp Pro Gly Pro Asn Gly Glu Thr Tyr Glu Asp Phe Asp Thr Arg Ile
            210                 215                 220

Leu Glu Val Arg Asn Val Phe Asn Met Thr Ala Lys Glu Gly Arg Lys
225                 230                 235                 240

Lys Ser Val Arg Val Leu Val Ala Val Gly Asn Gly Asn Gly Ala Ala
            245                 250                 255

Gly Phe Ala Ile Gly Lys Ala Ala Asp Arg Gly Asp Ala Phe Arg Lys
            260                 265                 270

Ala Lys Asn Arg Ala Ile His Tyr Leu His Tyr Ile Glu Arg Tyr Glu
            275                 280                 285

Gly His Thr Ile Phe His Asp Ile Ser Leu Arg Phe Lys Arg Thr Gln
            290                 295                 300

Ile Arg Met Lys Lys Gln Pro Arg Gly Tyr Gly Leu Arg Cys His Arg
305                 310                 315                 320

Ala Ile Ile Thr Ile Cys Arg Leu Ile Gly Ile Lys Asp Met Tyr Ala
                325                 330                 335

Arg Val Thr Gly Ser Met Asn Met Leu Asn Leu Thr Arg Gly Leu Phe
            340                 345                 350

His Gly Leu Ala Arg Gln Glu Thr His Gln His Leu Ala Asp Lys Lys
            355                 360                 365

Gly Leu His Val Val Glu Phe Arg Glu Glu Cys Gly Pro Leu Pro Ile
            370                 375                 380

Val Val Ala Ser Pro His Gly Ala Leu Ser Lys Glu Pro Glu Pro Glu
385                 390                 395                 400

Pro Glu Val Pro Asp Thr Lys Leu Asp Trp Gln Asp Val Lys Ala Met
                405                 410                 415

Gln Gly Leu Lys Arg Ser Val Trp Phe Asn Leu Lys Arg Pro Ala Thr
            420                 425                 430

<210> SEQ ID NO 5
<211> LENGTH: 336
<212> TYPE: PRT
<213> ORGANISM: Mus musculus

<400> SEQUENCE: 5

Met Ala Ala Val Arg Cys Leu Arg Arg Val Leu Ile His His Gln
1               5                   10                  15

Arg His Cys Leu Cys Lys Met Ala Ser Gln Ala Ser Leu Tyr Pro Cys
            20                  25                  30

Ser Val Asn Ser Leu Leu His Asn Arg His Phe Ala Ala Ala Ala
            35                  40                  45

Ala Ala Thr Lys Pro Ala Arg Lys Ile Lys Lys Gly Ala Lys Glu Lys
50                  55                  60

Thr Ser Asp Glu Lys Pro Val Asp Ile Glu Ile Lys Ser Tyr
65                  70                  75                  80

Thr Tyr Met Glu Ser Asp Pro Glu Asp Val Tyr Leu Lys Arg Leu
            85                  90                  95

Tyr Pro Arg Arg Ile Tyr Glu Val Glu Lys Ala Ile His Leu Leu Lys
                100                 105                 110

Lys Phe Gln Val Leu Asp Phe Thr Asn Pro Lys Gln Gly Val Tyr Leu
            115                 120                 125
```

```
Asp Leu Thr Leu Asp Met Ala Leu Gly Lys Lys Thr Val Glu Pro
    130                 135                 140

Phe Ala Ser Val Ile Ala Leu Pro His Leu Phe Ser Ser Glu Val Asn
145                 150                 155                 160

Lys Val Ala Val Phe Thr Ala Asn Ala Ser Glu Ile Lys Ile Ala Glu
                165                 170                 175

Glu Asn Gly Ala Ala Phe Ala Gly Gly Thr Asp Leu Val Lys Lys Ile
            180                 185                 190

Met Asp Asp Glu Val Val Asp Phe Tyr Val Ala Val Pro Glu Ile
        195                 200                 205

Met Gly Glu Leu Asn Pro Leu Arg Lys Leu Lys Lys Arg Phe Pro
    210                 215                 220

Lys Ala Thr Arg Asn Ser Ile Gly Arg Asp Ile Pro Lys Met Leu Glu
225                 230                 235                 240

Leu Phe Lys Thr Ala His Glu Ile Met Val Asp Glu Arg Gln Asn
                245                 250                 255

Phe Leu Ser Thr Lys Ile Ala Thr Leu Asp Met Pro Ser Asp Gln Ile
                260                 265                 270

Ala Ala Asn Leu Gln Ala Val Ile Asn Glu Val Cys Lys His Arg Pro
            275                 280                 285

Leu Asn Leu Gly Pro Phe Val Val Arg Ala Phe Leu Arg Ser Ser Thr
290                 295                 300

Ser Glu Gly Leu Leu Leu Lys Thr Asp Ser Leu Leu Pro Lys Glu Ala
305                 310                 315                 320

Lys Thr Thr Glu Ala Glu Thr Glu Glu Thr Gln Thr Ala Glu Ala Ala
                325                 330                 335

<210> SEQ ID NO 6
<211> LENGTH: 306
<212> TYPE: PRT
<213> ORGANISM: Mus musculus

<400> SEQUENCE: 6

Met Ala Leu Cys Ala Leu Thr Ser Ala Leu Arg Ser Leu Ser Leu Ala
1               5                   10                  15

Ser Ala Ala Ile Thr Ala Arg Val Pro Thr Leu Leu Pro Ala Ala Gln
                20                  25                  30

Ile Gln Ser Asn Val Leu Leu Gln Leu Pro Pro Ala Leu Val Ser Pro
            35                  40                  45

Ser Tyr Arg Pro Val His Met Ser Ala Asp Arg Ser Ala Lys Phe Val
50                  55                  60

Ser Trp Lys Ser Arg Thr Lys Tyr Thr Val Lys Pro Val Lys Met Arg
65                  70                  75                  80

Lys Ser Gly Gly Arg Asp His Thr Gly Arg Ile Arg Val His Gly Ile
                85                  90                  95

Gly Gly Gly His Lys Gln Asn Tyr Arg Met Ile Asp Phe Leu Arg Phe
            100                 105                 110

Arg Pro Glu Lys Glu Lys Ala Pro Glu Pro Phe Glu Glu Lys Val Val
        115                 120                 125

Val Val Arg Tyr Asp Pro Cys Arg Ser Ala Asp Ile Ala Leu Val Ala
    130                 135                 140

Gly Gly Ser Arg Lys Arg Trp Ile Ile Ala Thr Glu Asn Met Lys Ala
145                 150                 155                 160

Gly Asp Thr Ile Leu Asn Ser Asn His Ile Gly Arg Met Ala Val Ala
                165                 170                 175
```

Ala Gln Glu Gly Asp Ala His Pro Leu Gly Ala Leu Pro Val Gly Thr
            180                 185                 190

Leu Ile Asn Asn Val Glu Ser Glu Pro Gly Arg Gly Ala Gln Tyr Ile
            195                 200                 205

Arg Ala Ala Gly Thr Cys Gly Val Leu Leu Arg Lys Val Asn Gly Thr
210                 215                 220

Ala Ile Ile Gln Leu Pro Ser Lys Arg Gln Met Gln Val Leu Glu Ser
225                 230                 235                 240

Cys Thr Ala Thr Val Gly Arg Val Ser Asn Val Asn His Asn Gln Arg
                245                 250                 255

Val Ile Gly Lys Ala Gly Arg Asn Arg Trp Leu Gly Lys Arg Pro Asn
            260                 265                 270

Ser Gly Leu Trp Gln Arg Lys Gly Gly Trp Ala Gly Arg Lys Ile Arg
            275                 280                 285

Pro Leu Pro Pro Met Lys Ser Tyr Val Lys Leu Pro Ser Ala Ala Ala
            290                 295                 300

Gln Asn
305

<210> SEQ ID NO 7
<211> LENGTH: 29
<212> TYPE: DNA
<213> ORGANISM: Artificial Sequence
<220> FEATURE:
<223> OTHER INFORMATION: forward primer

<400> SEQUENCE: 7
gacaacgcgt aacaaaagag gggcgtcag                                29

<210> SEQ ID NO 8
<211> LENGTH: 30
<212> TYPE: DNA
<213> ORGANISM: Artificial Sequence
<220> FEATURE:
<223> OTHER INFORMATION: reverse primer

<400> SEQUENCE: 8
gacactcgag ccctgagaaa ccaagtcagc                               30

<210> SEQ ID NO 9
<211> LENGTH: 30
<212> TYPE: DNA
<213> ORGANISM: Artificial Sequence
<220> FEATURE:
<223> OTHER INFORMATION: forward primer

<400> SEQUENCE: 9
gacaacgcgt ctttccggtc tgatctccag                               30

<210> SEQ ID NO 10
<211> LENGTH: 29
<212> TYPE: DNA
<213> ORGANISM: Artificial Sequence
<220> FEATURE:
<223> OTHER INFORMATION: reverse primer

<400> SEQUENCE: 10
gacactcgag gtaccgtctg ctccaccac                                29

MITOCHONDRIAL RIBOSOMAL PROTEINS AS AGING REGULATORS

CROSS-REFERENCE TO RELATED APPLICATIONS

This application is the U.S. national stage application of International Patent Application No. PCT/IB2012/054206, filed Aug. 20, 2012, which claims the benefit of U.S. Provisional Patent Application No. 61/524,889, filed Aug. 18, 2011.

FIELD OF THE INVENTION

The present invention relates to methods of increasing lifespan, inhibiting or delaying aging, and/or preventing an age-related disease or a mitochondrial disease in a subject, comprising inducing a nuclear-mitochondrial OXPHOS protein dyssynchrony, as well as methods for screening agents that are able to increase lifespan, inhibit or delay aging, and/or prevent or treat an age-related disease or a mitochondrial disease, in a subject.

BACKGROUND OF THE INVENTION

Lifespan regulation is a complex process that is coordinated by divergent pathways, including DNA damage, oxidative stress, and metabolic networks (Houtkooper et al., 2010, *Cell* 142, 9). It has been established by gain- and loss-of-function studies, especially in *C. elegans* and *D. melanogaster*, but also in mice, that caloric excess pathways, such as the insulin/IGF1 signaling pathway and the mammalian target of rapamycin (mTOR), decrease lifespan (Harrison et al., 2009, *Nature* 460, 392-395; Bjedov et al., 2010, *Cell Metab* 11, 35; Zid et al., 2009, *Cell* 139, 149; Selman et al., 2009, *Science* 326, 140), whereas the caloric restriction pathways, for instance AMP-activated protein kinase (AMPK) and sirtuins, tend to increase lifespan (Mair et al., 2011, *Nature* 470, 404-408; Anisimov et al., 2008, *Cell Cycle* 7, 2769). Whether or not such genes also contribute to natural lifespan is, however, not understood.

Additionally, in mouse, AMPK has been connected with sirtuin 1 (SIRT1) (Canto et al., 2009, *Nature* 458, 1056-1060) and peroxisome proliferator-activated receptor-γ coactivator (PGC-1)-α signaling (Canto et al., 2009, supra; Canto et al., 2010, *Cell Metab* 11, 213-219) consolidating the link of this system with mitochondrial metabolism, notably mitochondrial respiration. It is still debated, however, how mitochondrial function impacts aging, as both inhibiting and stimulating mitochondrial metabolism seems to enhance lifespan (discussed in Houtkooper et al., 2010, supra; Kenyon, 2010, *Nature* 464, 504-512).

Aging and the diseases associated with it are a heavy burden on society. The current increase in life expectancy not only impacts on our social systems, but also goes hand in hand with the emergence of common chronic diseases, including those of the nervous, immune, and cardio-metabolic systems, which often reach epidemic proportions. In this respect it is important to understand the natural aging process and to elucidate where lifestyle and/or pharmacological interventions can have an impact. In recent years, many novel therapeutic options have been suggested to prevent aging-associated diseases. Although some of these pharmaceutical interventions were shown to extend lifespan, even in mammals (Harrison et al., 2009, supra; Pearson et al., 2008, *Cell Metab* 8, 157-168), there is still a need for identification of novel compounds that have the ability to increase lifespan and, thus, be useful for delaying aging and/or preventing or treating age-related diseases and disorders.

The present invention solves this problem by identifying a novel target that functions as a longevity regulator and is conserved from *Caenorhabditis elegans* to mammals.

SUMMARY OF THE INVENTION

The present invention is directed towards a novel target that functions as a longevity regulator and is conserved from *Caenorhabditis elegans* to mammals, as well as methods and uses thereof.

A first aspect of the invention provides a method of increasing lifespan in a subject, comprising inducing a nuclear-mitochondrial OXPHOS protein dyssynchrony, including for instance by inhibiting the mitochondrial translation machinery function, in said subject.

A second aspect of the invention relates to a method of inhibiting or delaying the aging process in a subject comprising inducing a nuclear-mitochondrial OXPHOS protein dyssynchrony, including for instance by inhibiting the mitochondrial translation machinery function in said subject.

A third aspect of the invention relates to a method of treating, preventing, or delaying, an age-related disease or disorder or a mitochondrial disease or disorder, in a subject, comprising administering in a subject in need thereof an effective amount of an agent or composition that induces a nuclear-mitochondrial OXPHOS protein dyssynchrony, including for instance by inhibiting the mitochondrial translation machinery function, in said subject.

A fourth aspect of the invention relates to the use of an agent or composition that induces a nuclear-mitochondrial OXPHOS protein dyssynchrony, including for instance by inhibiting the mitochondrial translation machinery function, in a subject, in the manufacture of a medicament for increasing lifespan, inhibiting or delaying the aging process, and/or treating, preventing, or delaying, an age-related disease or disorder or a mitochondrial disease or disorder, in said subject.

A fifth aspect of the invention resides in an agent or composition that induces a nuclear-mitochondrial OXPHOS protein dyssynchrony, including for instance by inhibiting the mitochondrial translation machinery function in a subject, for use in increasing lifespan, inhibiting or delaying the aging process, and/or treating, preventing, or delaying, an age-related disease or disorder or a mitochondrial disease or disorder, in said subject.

A sixth aspect of the invention relates to a method of screening a compound for its ability to increase lifespan, inhibit or delay the aging process, and/or prevent, treat, or delay an age-related disease or disorder or a mitochondrial disease or disorder, in a subject, comprising:
  a) Contacting a cell or a non-human subject with a test compound; and
  b) Measuring the mitochondrial unfolded protein response ($UPR^{mt}$) in the presence and in the absence of the test compound in said cell or said non-human subject,
  wherein a test compound that modulates the $UPR^{mt}$ determined in step b) in the cell or non-human subject indicates a compound that is able to increase lifespan, inhibit or delay the aging process, and/or prevent, treat, or delay an age-related disease or disorder or a mitochondrial disease or disorder.

A seventh aspect of the invention relates to a method of screening a compound for its ability to increase lifespan, inhibit or delay the aging process, and/or prevent, treat, or delay an age-related disease or disorder or a mitochondrial disease or disorder, in a subject, comprising:
- a) Contacting a cell or a non-human subject with a test compound; and
- b) Measuring the ratio between (i) the expression and/or activity of nuclear DNA-encoded OXPHOS proteins and (ii) the expression and/or activity of mitochondrial DNA-encoded OXPHOS proteins, in the presence and in the absence of the test compound in said cell or said non-human subject, wherein a test compound that modulates the ratio determined in step b) in the cell or non-human subject indicates a compound that is able to increase lifespan, inhibit or delay the aging process, and/or prevent, treat, or delay an age-related disease or disorder or a mitochondrial disease or disorder.

An eighth aspect of the invention relates to an ex-vivo method of prognosis and/or diagnosis of premature aging, or age-related disease or disorder, or mitochondrial disease or disorder, in a patient, comprising:
- a) providing a body sample from said patient;
- b) measuring the mitochondrial unfolded protein response ($UPR^{mt}$) in said sample;
- c) comparing the level of $UPR^{mt}$ determined in step b) with a reference value;

wherein a level of $UPR^{mt}$ determined in step b) that differs from the reference value is indicative of premature aging, development of an age-related disease or disorder, or of a mitochondrial disease or disorder.

A ninth aspect of the invention relates to an ex-vivo method of prognosis and/or diagnosis of premature aging, or age-related disease or disorder, or mitochondrial disease or disorder, in a patient, comprising:
- a) providing a body sample from said patient;
- b) measuring the ratio between (i) the expression and/or activity of nuclear DNA-encoded OXPHOS proteins and (ii) the expression and/or activity of mitochondrial DNA-encoded OXPHOS proteins in said sample;
- c) comparing the ratio determined in step b) with a reference value;

wherein a ratio determined in step b) that differs from the reference value is indicative of premature aging, development of an age-related disease or disorder, or of a mitochondrial disease or disorder.

A tenth aspect of the invention relates to a kit for carrying out any of the methods and uses mentioned above.

Other features and advantages of the invention will be apparent from the following detailed description.

DESCRIPTION OF THE FIGURES

FIG. 4A Knockdown of MRP genes induced $UPR^{mt}$, as determined using the hsp-6::GFP reporter, similarly to the knockdown of cco-1. FIG. 4B Quantification of $UPR^{mt}$ signal upon knockdown of mrps-5, mrpl-1 or mrpl-2, as well as cco-1. FIG. 4C $UPR^{ER}$ was not induced by knockdown of mrps-5 or cco-1. The ER stress inducer tunicamycin is used as a positive control. FIG. 5(A-F) Ubl-5 epistasis. Double RNAi of mrps-5 and ubl-5 partially prevented lifespan extension (FIG. 5A), reduction in respiration (FIG. 5B), and $UPR^{mt}$ (FIG. 5C), compared to mrps-5 RNAi alone. Knockdown of cco-1 in combination with ubl-5 showed identical effects (FIG. 5(D-F)). FIG. 6 Ubl5 expression correlated with MRPs (e.g. Mrpl2 and Mrpl14, and Mrpl34) in various tissues of mouse GRPs, such as hippocampus of the BXD strains and white adipose tissue of an F2 intercross. *p≤0.05; ***p≤0.001.

DETAILED DESCRIPTION OF THE INVENTION

Figure 1:
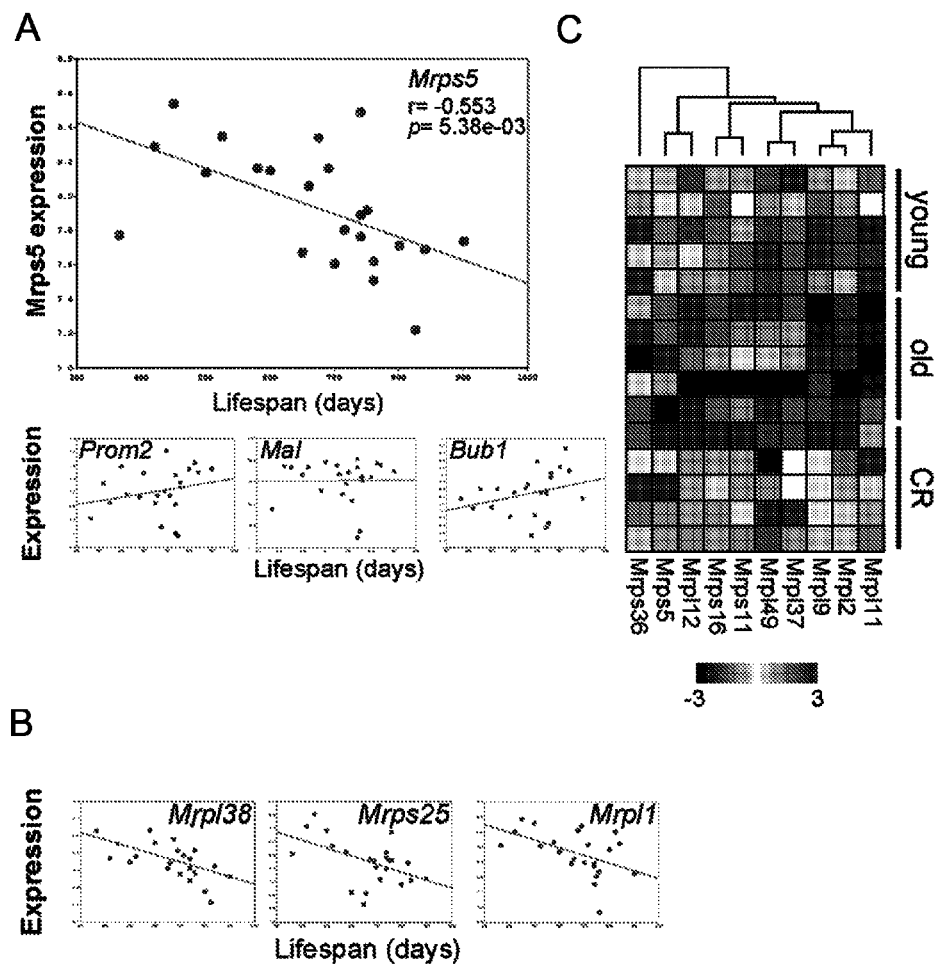
FIG. 1 shows lifespan regulation in BXD recombinant inbred mice. A) Expression of Mrps5, which is located in the longevity associated chromosome 2 region, shows strong correlation with longevity (Pearson's r=−0.553, p=5.38e-03), whereas other genes in this region, e.g. Prom2, Mal, Nphp1, and Bub1 are not correlated with longevity. (B) Other mitochondrial ribosomal proteins are also correlated with longevity. Mrpl38: r=−0.534, p=7.78e-03; Mrps25: r=−0.503, p=1.33e-02; Mrpl1: r=−0.486, p=1.76e-02. (C) One-way hierarchical clustering showing MRP gene expression differences between young (5 months), old (25 months) and caloric restricted (CR)C57BL/6N mice from published microarray datasets.

The term "subject" as used herein refers to multicellular organisms including invertebrate animal-models such as *Caenorhabditis elegans* and *Drosophila*, as well as other animals such as mammals. For example, mammals contemplated by the present invention include human, primates, domesticated animals such as cattle, sheep, pigs, horses, laboratory rodents including rat and mouse.

"Lifespan" or "longevity" are used interchangeably herewith. These terms refer to the maximum age of an animal as measured by a time scale, such as months and years.

As used herewith, the term "nuclear-mitochondrial OXPHOS protein dyssynchrony" refers to an alteration of the ratio between (i) the expression and/or activity of nuclear DNA-encoded OXPHOS proteins and (ii) the expression and/or activity of mitochondrial DNA-encoded OXPHOS proteins. In the present application, "dyssynchrony" covers both an increase or a decrease of the above-mentioned ratio. "Nuclear-mitochondrial OXPHOS protein dyssynchrony"

can be induced by various mechanisms including, for instance, by altering mitochondrial translation, nuclear translation, nuclear DNA-encoded OXPHOS translocation to the mitochondria, mitochondrial biogenesis. For example, nuclear-mitochondrial OXPHOS protein dyssynchrony, whereby the dyssynchrony consists of an increase in the above-mentioned ratio, could result from any one of the following: inhibiting mitochondrial translation machinery, increasing the nuclear DNA-encoded OXPHOS proteins while maintaining the mitochondrial DNA-encoded OXPHOS proteins, increasing the nuclear DNA-encoded OXPHOS proteins while reducing the mitochondrial DNA-encoded OXPHOS proteins, increasing mitochondrial import of nuclear DNA-encoded OXPHOS proteins. For example, nuclear-mitochondrial OXPHOS protein dyssynchrony, whereby the dyssynchrony consists of a decrease in the above-mentioned ratio, could result from any one of the following: inducing mitochondrial translation machinery, reducing mitochondrial biogenesis, reducing nuclear DNA-encoded OXPHOS translation and/or inducing mitochondrial DNA-encoded OXPHOS proteins translation, reducing the import of nuclear DNA-encoded OXPHOS proteins into the mitochondria. In the present application, the abbreviations "nDNA" refers to nuclear DNA and "mtDNA" refers to mitochondrial DNA, respectively.

"OXPHOS proteins" refers to the proteins involved in the oxidative phosphorylation (OXPHOS), which is the metabolic pathway that uses energy released by the oxidation of nutrients to produce adenosine triphosphate (ATP). OXPHOS proteins comprise nuclear DNA-encoded OXPHOS proteins which translocate to and function in synchrony with the mitochondrial DNA-encoded OXPHOS proteins. Examples of nuclear DNA-encoded OXPHOS proteins include ATP5A or ATP5 (Subunit 5 of the stator stalk of mitochondrial FIF0 ATP synthase), UQCRC2 (Cytochrome b-c1 complex subunit 2), and SDHB (succinate dehydrogenase [ubiquinone] iron-sulfur subunit). Examples of mitochondrial DNA-encoded OXPHOS proteins include MTCO1 (Mitochondrially encoded cytochrome c oxidase I).

"Mitochondrial translation machinery" refers to the cell components involved in the protein translation process and its regulation, in the mitochondria. This term includes the ribosome subunits, the proteins comprised in the ribosome subunits, the tRNA, the aminoacyltRNA, which are present in the mitochondria.

"Inhibition of the mitochondrial translation machinery function" refers to the inhibition of the translation process in the mitochondria, including the inhibition of any one of the initiation step, elongation step and termination step. Inhibition of the mitochondrial translation machinery can be tested by standard method in the field, such as, for instance, the method described in Leary and Sasarman (in Jeffrey A. Stuart (Ed), 2009, Mitochondrial DNA, Methods and Protocols, 554, 143-162).

The terms "inhibitor", "antagonist", or "agent or composition that inhibits" as used herein refer to any substances that are able to totally or partially inhibit, block, attenuate, or interfere with the functioning of the mitochondrial translation machinery. Thus, the terms "inhibitor", "antagonist", or "agent or composition that inhibits", are intended to include, but are not limited to, molecules which prevent or reduce the initiation step, elongation step or termination step of the protein translation process in the mitochondria, and/or reduce the expression of the gene encoding a mitochondrial ribosomal protein or neutralize the activity of a mitochondrial ribosomal protein. For example, inhibitors include small molecules (such as antibiotics), peptides, peptidomimetics, chimaeric proteins, natural or unnatural proteins, nucleic acid derived polymers (such as DNA and RNA aptamers, siNAs, siRNAs, shRNAs, PNAs, or LNAs), fusion proteins (such as fusion proteins with MRP antagonizing activities), antibody antagonists (such as neutralizing anti-MRP antibodies), or gene therapy vectors driving the expression of MRP inhibitors.

"Mitochondrial ribosomal proteins" or "MRPs" refers to proteins encoded by nuclear genes which help in protein synthesis within the mitochondrion. In mammals, mitochondrial ribosomes (mitoribosomes) consist of a small 28S subunit and a large 39S subunit. They have an estimated 75% protein to rRNA composition compared to prokaryotic ribosomes, where this ratio is reversed. Another difference between mammalian mitoribosomes and prokaryotic ribosomes is that the latter contain a 5S rRNA. Estimates for the number of proteins in mammalian mitochondrial ribosomes have ranged from about 85 to more than 100 (O'Brien, 2002, Gene 286, 73-79). Among different species, the proteins comprised in the mitoribosome differ greatly in sequence, and sometimes in biochemical properties. Examples of MRP in various organisms are provided in Table 1 below. As defined herewith MRP covers any member of the MRP family in any species. Preferred MRP are from mammals, more preferably from humans. This term also covers, in particular, any one of the MRP mentioned in Table 1, as well as a MRP of amino acid sequence SEQ ID NO: 1, SEQ ID NO: 2, SEQ ID NO: 3, SEQ ID NO: 4, SEQ ID NO: 5, and/or SEQ ID NO: 6, or any homologous protein thereof

TABLE 1

Examples of mitochondrial ribosomal proteins (MRP) from different organisms. The references in Uniprot database are indicated in brackets.

| Yeast MRP | C. elegans MRP | Mouse MRP | Human MRP |
|---|---|---|---|
| Mrps5 (P33759) | Mrps5 (Q93425) | Mrps5 (Q99N87) | Mrps5 (P82675) |
| Mrpl1 (Q04599) | F33D4.5 (Q7KPW7) | Mrpl1 (Q99N96) | Mrpl1 (Q9BYD6) |
| Mrpl2 (P12687) | F56B3.8 (O45110) | Mrpl2 (Q9D773) | Mrpl2 (Q5T653) |
| | | Mrpl11 (Q9CQF0) | Mrps6 (P82932) |
| | | Mrpl9 (Q99N94) | Mrps7 (Q9Y2R9) |
| | | Mrpl37 (Q921S7) | Mrps10 (P82664) |
| | | Mrpl49 (Q9CQ40) | Mrps11 (P82912) |
| | | Mrps11 (Q9DCA2) | Mrps15 (P82914) |
| | | Mrps16 (Q9CPX7) | Mrps16 (Q9Y3D3) |
| | | Mrpl12 (Q9DB15) | Mrps17 (Q9Y2R5) |
| | | Mrps36 (Q9CQX8) | Mrps18a (Q9NVS2) |
| | | | Mrps18b (Q9Y676) |
| | | | Mrps18c (Q9Y3D5) |

TABLE 1-continued

Examples of mitochondrial ribosomal proteins (MRP) from different organisms.
The references in Uniprot database are indicated in brackets.

| Yeast MRP | C. elegans MRP | Mouse MRP | Human MRP |
| --- | --- | --- | --- |
| | | | Mrps21 (P82921) |
| | | | Mrps22 (P82650) |
| | | | Mrps23 (Q9Y3D9) |
| | | | Mrps24 (Q96EL2) |
| | | | Mrps24 (Q96EL2) |
| | | | Mrps25 (P82663) |
| | | | Mrps29 (P51398) |
| | | | Mrps31 (Q92665) |
| | | | Mrps33 (Q9Y291) |
| | | | Mrps35 (P82673) |
| | | | Mrps36 (P82909) |
| | | | Mrpl3 (P09001) |
| | | | Mrpl9 (Q9BYD2) |
| | | | Mrpl11 (Q9Y3B7) |
| | | | Mrpl14 (Q6P1L8) |
| | | | Mrpl15 (Q9P015) |
| | | | Mrpl20 (Q9BYC9) |
| | | | Mrpl22 (Q9NWU5) |
| | | | Mrpl30 (Q8TCC3) |
| | | | Mrpl32 (Q9BYC8) |
| | | | Mrpl35 (Q9NZE8) |
| | | | Mrpl36 (Q9P0J6) |
| | | | Mrpl42 (Q9Y6G3) |
| | | | Mrpl45 (Q9BRJ2) |
| | | | Mrpl48 (Q96GC5) |
| | | | Mrpl49 (Q13405) |
| | | | Mrpl50 (Q8N5N7) |
| | | | Mrpl51 (Q4U2R6) |
| | | | Mrpl53 (Q96EL3) |
| | | | Mrp63 (Q9BQC6) |

The term "MRP antibody" or "anti-MRP antibody" as used herein refers to any antibody or variant form thereof, including but not limited to, antibody fragment, domain antibody or single chain antibody capable of selectively binding to MRP protein or fragment thereof. In particular, MRP antibodies include a MRP antibody able to bind to the epitopes of a mammalian, notably human, MRP, in particular any one of the MRP mentioned in Table 1, preferably a MRP of amino acid sequence SEQ ID NO: 1, SEQ ID NO: 2, SEQ ID NO: 3, SEQ ID NO: 4, SEQ ID NO: 5, and/or SEQ ID NO: 6, or any homologous protein thereof. A MRP antibody includes murine, chimeric, humanized, or fully human antibodies, genetically engineered or bispecific or multispecific antibodies as well as fragments thereof such as single chain antibodies (scFv) or domain antibodies against MRP protein or fragment thereof and the like. Antibodies of this invention may be monoclonal or polyclonal antibodies, or fragments or derivatives thereof having substantially the same antigen specificity. The term "selectively" indicates that the antibodies preferentially recognize and/or bind the target polypeptide or epitope, i.e., with a higher affinity than to any other antigen or epitope, i.e. the binding to the target polypeptide can be discriminated from non-specific binding to other antigens. The binding affinity of an antibody can be readily determined by one of ordinary skill in the art, for example, by Scatchard analysis (Scatchard et al., 1949, *Ann. N.Y. Acad.* 51, 660-672).

The term "antibody antagonist" as used herein refers to any antibody or variant form thereof, including but not limited to, antibody fragment, domain antibody or single chain antibody capable of reducing the activity of the mitochondrial translation machinery or reducing the activity of the mitochondrial ribosomal protein (MRP). Antibody antagonists include antibodies in a conventional immunoglobulin format (IgA, IgD, IgE, IgG, IgM), and also fragments thereof or any other "antibody-like" format that binds to mammalian, notably human, MRP (for example, a single chain Fv fragment, a fragment Fc, a Fd fragment, a Fab fragment, a Fab' fragment, a $F(ab)_2$ fragment, chimeric antibodies, diabodies, domain antibodies (dAbs) such as described in Holliger et al. (2005, *Nature Biotechnology,* 23(9), 1126-11369) and polypeptides that contain at least a portion of an immunoglobulin that is sufficient to confer specific antigen-binding to the polypeptide (e.g., immunoadhesins). The terms Fv, Fc, Fd, Fab, or $F(ab)_2$ are used with their standard meanings (Harlow et al., 1988, *Antibodies: A Laboratory Manual, Cold Spring Harbor Laboratory Press*; Dec. 1, 1988. ISBN 978-0879693145). Antibodies according to the invention can be generated by immunization of a suitable host (e.g., vertebrates, including humans, mice, rats, sheep, goats, pigs, cattle, horses, reptiles, fishes, amphibians, and in eggs of birds, reptiles and fish). Determination of immunoreactivity with an immunogenic MRP polypeptide may be made by any of several methods well known in the art, including, e.g., immunoblot assay and ELISA. Modification of such antibodies into therapeutically useful derivatives may he made by methods as described in *Handbook of Therapeutic Antibodies*. Stefan Dübel (Ed: Jan. 2007. ISBN: 978-3-527-31453-9. The term "anti-MRP antibody" may be a neutralizing anti-MRP antibody or a fragment thereof, such as a murine antibody, a humanized antibody such as a humanized variant of a murine antibody, a human antibody, or a fragment thereof A non-limiting list of examples of anti-MRP antibody include known commercial antibodies such as: anti-MRPS5 (301-315) antibody produced in rabbit (Sigma SAB1101981), anti-MRPL2 antibody produced in rabbit (Sigma HPA007455), anti-MRPL1 antibody (Abcam ab67245); and humanized variants thereof.

The term "small inhibitory nucleic acids" (siNAs) refers to short nucleic acids used in strategies targeting mRNA recognition and its downregulation based on their antisense action. This term covers antisense oligonucleotides, catalytic nucleic acids such as ribozymes and deoxyribozymes, as well as small interfering RNAs (siRNAs).

The term "siRNA" refers to small interfering RNA which are single or double stranded RNA (about 19-23 nucleotides) able to knock down or silence a targeted mRNA from a target gene. Artificial siRNAs can be either chemically synthesized as oligonucleotides or cloned into a plasmid or a virus vector (adenovirus, retrovirus or lentivirus) as short hairpin RNAs (shRNAs) to generate a transient or stable transfection in any type of cells (Martin et al., 2007, *Ann. Rev. Genomics Hum. Genet.*, 8:81-108; Kolfschoten et al., 2007, *Nat. Clin. Pract. Endocrinol. Metab.*, 3(12):827-34; Huang et al., 2008, *Expert. Opin. Ther. Targets*, 12(5), 637-645).

The term "peptidomimetic" is defined as a peptide analog containing non-peptidic structural elements, which peptide is capable of mimicking or antagonizing the biological action(s) of a natural parent peptide. A peptidomimetic lacks classical peptide characteristics such as enzymatically scissile peptide bonds.

The expression "antibiotics that target bacterial translation" refers to antibiotics which inhibit the translation process in bacteria. The inhibition can take place, for instance, by binding of the antibiotic to the bacterial 30S ribosomal subunit or to the bacterial 50S ribosomal subunit, inhibiting the translocation of the peptidyl-tRNA from the A-site to the P-site, and/or inhibiting the binding of aminoacyl-tRNA to the mRNA-ribosome complex. Antibiotics that target bacterial translation include antibiotics of various classes, such as, for instance, the aminoglycosides (e.g. amikacin, gentamicin, kanamycin, neomycin, netilmicin, tobramycin, paromomycin), lincosamides (e.g. clindamycin, lincomycin), macrolides (e.g. azithromycin, clarithromycin, dirithromycin, erythromycin, roxithromycin, troleandomycin, telithromycin, spectinomycin), tetracyclines (e.g. demeclocycline, doxycycline, minocycline, oxytetracycline, tetracycline), chloramphenicol and thiamphenicol. Also covered by this expression, are derivatives or analogs of the above-mentioned antibiotics. Antibiotics that target bacterial translation are also expected to inhibit the mitochondrial translation machinery in eukaryotes (Mc Kee et al. 2006, *Antimicrobial agents and Chemotherapy*, 2042-2049). In contrast, antibiotics that target the bacterial cell wall synthesis (such as those of the classes of carbacephem, carbapenems, cephalosporins, monobactams, penicillins), antibiotics that inhibit DNA replication and transcription (such as those of the class of the quinolones), and antibiotics that inhibit cell division (such as those of the class of the sulphonamides), are not covered by the term "antibiotics that target bacterial translation".

"Homologous protein" means a protein from a species having a similar amino acid sequence as another protein from a different species and, thus, both proteins are likely to derive from a common ancestor.

As defined herewith "mitochondrial unfolded protein response" or "UPR$^{mt}$" refers to a cellular stress response related to the mitochondria. The UPR$^{mt}$ is induced by mitochondrial stress signals subsequently activating a nuclear transcriptional response. For example, in *C. elegans*, expression of mitochondrial chaperones HSP-6 (mitochondrial HSP-70 in mammals) and HSP-60 is increased, aimed to restore protein homeostasis (also known as proteasis) in mitochondria.

The term "regulatory sequence" encompasses a sequence that regulates the transcription and translation of a gene and, thus, controls the expression of said gene. The regulatory sequence optionally contains a promoter, an enhancer, and/or a poly-adenylation signal. As used herein, a coding sequence and regulatory sequences are said to be "operably" linked when they are covalently linked in such a way as to place the expression or transcription of the coding sequence under the influence or control of the regulatory sequence(s). If it is desired that the coding sequence be translated into a functional protein, two DNA sequences are said to be operably linked if induction of a promoter in the 5' regulatory sequence results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a coding sequence if the promoter region were capable of effecting transcription of that DNA sequence such that the resulting transcript can be translated into the desired protein or polypeptide.

As defined herewith, "age-related disease or disorder" refers to a disease or disorder generally observed in older subjects. In mammals, in particular in humans, it includes common metabolic, inflammatory, cardiovascular and neurodegenerative diseases, as well as most cancers that occur in older people. Examples of age-related diseases or disorders include Parkinson's disease, Alzheimer's disease, obesity, type 2 diabetes, atherosclerosis, reduced kidney function (renal insufficiency), reduced skeletal muscle strength (sarcopenia), chronic inflammatory diseases (arthritis, arthrosis), anemia, cancers, hearing and vision loss (e.g. age-related macular degeneration and deafness).

As defined herewith, "mitochondrial diseases or disorders" refer to diseases or disorders in which mitochondrial function is perturbed, either by inherited genetic mutation or by acquired mitochondrial malfunction. Genetic mitochondrial diseases are caused by inherited mutations in nuclear or mitochondrial DNA that result in perturbed mitochondrial function. Non-inherited mitochondrial diseases include diseases caused by external factors impacting mitochondrial function. These include, but are not limited to, Alzheimer disease, Parkinson disease, Huntington disease, and certain types of blindness and deafness. Mitochondrial diseases take on unique characteristics both because of the way the diseases are often inherited and because mitochondria are so critical to cell function. The subclass of these diseases that have neuromuscular disease symptoms are often called a mitochondrial myopathy. Examples of genetic mitochondrial diseases or disorders include Leber's hereditary optic neuropathy, Leigh syndrome, mitochondrial myopathies, Neuropathy ataxia retinitis pigmentosa and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), and mtDNA depletion such as mitochondrial neurogastrointestinal encephalomyopathy (MNGIE).

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, i.e., arresting its development; or relieving the disease, i.e., causing regression of the disease and/or its symptoms or conditions such as improvement or remediation of damage. In particular, the methods, uses, formulations and compositions according to the invention are useful in the treatment of age-related diseases and disorders and/or in the prevention of evolution of an age-related diseases and disorders into its final stage and possibly death. When applied to an age-related disease or disorder such as, for instance, Alzheimer's or Parkinson's disease, prevention of a disease or disorder includes the prevention of the appearance or development of said disease in an individual identified as at risk of developing said disease, for instance due to past occurrence of said disease in the circle of the individual's relatives. Also covered by the terms "prevention/treatment" of an age-related disease is the stabilization of an already diagnosed age-related disease or disorder in an individual. By "stabilization", it is meant the prevention of evolution of said disease into advanced or final stage in subject with the disease at an early stage. The term "effective amount" as used herein refers to an amount of at least one agent, composition or pharmaceutical formulation thereof according to the invention, that elicits the biological or medicinal response in a tissue, system, animal or human that is being sought. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of agent or composition sufficient to reduce the progression of the disease.

The term "efficacy" of a treatment according to the invention can be measured based on changes in the course of disease in response to a use or a method according to the invention. For example, the efficacy of a treatment of an age-related disease or disorder can be measured by a reduction of the symptoms of the disease or disorder, for instance increased muscle strength, better glucose tolerance, increased cold tolerance, increased exercise capacity.

Methods and Uses According to the Invention Related to Lifespan Expansion and Treatment of Diseases In one embodiment, the invention relates to a method of increasing lifespan in a subject, comprising inducing a nuclear-mitochondrial OXPHOS protein dyssynchrony in said subject.

In a particular embodiment, the invention relates to a method of increasing lifespan in a subject, comprising inhibiting the mitochondrial translation machinery function in said subject.

In a further embodiment, the invention relates to a method of inhibiting or delaying the aging process in a subject comprising inducing a nuclear-mitochondrial OXPHOS protein dyssynchrony in said subject.

In a particular embodiment, the invention relates to a method of inhibiting or delaying the aging process in a subject comprising inhibiting the mitochondrial translation machinery function in said subject.

In another embodiment, the invention relates to a method of treating, preventing, or delaying, an age-related disease or disorder in a subject, comprising administering in a subject in need thereof an effective amount of an agent or composition that induces a nuclear-mitochondrial OXPHOS protein dyssynchrony in said subject, preferably in specific tissue(s) and/or organ(s) of said subject.

In a particular embodiment, the invention relates to a method of treating, preventing, or delaying, an age-related disease or disorder in a subject, comprising administering in a subject in need thereof an effective amount of an agent or composition that increases the ratio between the expression and/or activity of (i) nuclear-mitochondrial OXPHOS protein and (ii) mitochondrial OXPHOS proteins in said subject, preferably in specific tissue(s) and/or organ(s) of said subject.

In an alternative particular embodiment, the invention relates to a method of treating, preventing, or delaying, an age-related disease or disorder in a subject, comprising administering in a subject in need thereof an effective amount of an agent or composition that reduces the ratio between the expression and/or activity of (i) nuclear-mitochondrial OXPHOS proteins and (ii) mitochondrial OXPHOS proteins in said subject, preferably in specific tissue(s) and/or organ(s) of said subject.

In another embodiment, the invention relates to a method of treating, preventing, or delaying, an age-related disease or disorder in a subject, comprising administering in a subject in need thereof an effective amount of an agent or composition that inhibits the mitochondrial translation machinery function in said subject, preferably in specific tissue(s) and/or organ(s) of said subject.

In a still other embodiment, the invention relates to a method of treating, preventing, or delaying, an age-related disease or disorder in a subject, comprising administering in a subject in need thereof an effective amount of an antibiotic that targets bacterial translation such as tetracycline, doxycycline or chloramphenicol.

In a still other embodiment, the invention relates to a method of treating, preventing, or delaying, an age-related disease or disorder in a subject, comprising administering in a subject in need thereof an effective amount of tetracycline.

In a still other embodiment, the invention relates to a method of treating, preventing, or delaying, an age-related disease or disorder in a subject, comprising administering in a subject in need thereof an effective amount of doxycycline.

In a still other embodiment, the invention relates to a method of treating, preventing, or delaying, an age-related disease or disorder in a subject, comprising administering in a subject in need thereof an effective amount of chloramphenicol.

In a preferred aspect of the methods according to the invention, said disease or disorder is selected among Parkinson's disease, Alzheimer's disease, obesity, type 2 diabetes, atherosclerosis, reduced kidney function (renal insufficiency), reduced skeletal muscle strength (sarcopenia), chronic inflammatory diseases (arthritis, arthrosis), anemia, cancers, hearing and vision loss (e.g. age-related macular degeneration and deafness).

In another embodiment, the invention relates to a method of treating, preventing, or delaying, a mitochondrial disease or disorder in a subject, comprising administering in a subject in need thereof an effective amount of an agent or composition that induces a nuclear-mitochondrial OXPHOS protein dyssynchrony in said subject, preferably in specific tissue(s) and/or organ(s) of said subject.

In a particular embodiment, the invention relates to a method of treating, preventing, or delaying, a mitochondrial disease or disorder in a subject, comprising administering in a subject in need thereof an effective amount of an agent or composition that increases the ratio between the expression and/or activity of (i) nuclear-mitochondrial OXPHOS proteins and (ii) mitochondrial OXPHOS proteins in said subject, preferably in specific tissue(s) and/or organ(s) of said subject.

In an alternative particular embodiment, the invention relates to a method of treating, preventing, or delaying, a mitochondrial disease or disorder in a subject, comprising administering in a subject in need thereof an effective amount of an agent or composition that reduces the ratio between the expression and/or activity of (i) nuclear-mitochondrial OXPHOS proteins and (ii) mitochondrial OXPHOS proteins in said subject, preferably in specific tissue(s) and/or organ(s) of said subject.

In another embodiment, the invention relates to a method of treating, preventing, or delaying, a mitochondrial disease or disorder in a subject, comprising administering in a subject in need thereof an effective amount of an agent or composition that inhibits the mitochondrial translation machinery function in said subject, preferably in specific tissue(s) and/or organ(s) of said subject.

In a still other embodiment, the invention relates to a method of treating, preventing, or delaying, a mitochondrial disease or disorder in a subject, comprising administering in a subject in need thereof an effective amount of an antibiotic that targets bacterial translation such as tetracycline, doxycycline or chloramphenicol.

In a still other embodiment, the invention relates to a method of treating, preventing, or delaying, a mitochondrial disease or disorder in a subject, comprising administering in a subject in need thereof an effective amount of tetracycline.

In a still other embodiment, the invention relates to a method of treating, preventing, or delaying, a mitochondrial disease or disorder in a subject, comprising administering in a subject in need thereof an effective amount of doxycycline.

In a still other embodiment, the invention relates to a method of treating, preventing, or delaying, a mitochondrial disease or disorder in a subject, comprising administering in a subject in need thereof an effective amount of chloramphenicol.

In a preferred aspect of the methods according to the invention, said mitochondrial disease or disorder is selected among Alzheimer disease, Parkinson disease, Huntington disease, certain types of blindness and deafness, Leber's hereditary optic neuropathy, Leigh syndrome, mitochondrial myopathies, Neuropathy ataxia retinitis pigmentosa and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), and mtDNA depletion such as mitochondrial neurogastrointestinal encephalomyopathy (MNGIE).

In a preferred embodiment, the preceding methods according to the invention comprise inhibiting the mitochondrial translation machinery function mainly in specific tissue(s) and/or organ(s) of the subject to be treated, preferably in liver, muscle, fat, endocrine, and sensory-nervous tissues.

In a specific aspect, the methods according to the invention comprise inhibiting the expression of at least one gene encoding a mitochondrial ribosomal protein and/or the activity of at least one mitochondrial ribosomal protein, in the subject. More preferably, said mitochondrial ribosomal protein is selected among MRPS5, MRPL1 and/or MRPL2, still more preferably said mitochondrial ribosomal protein has any one of the amino acid sequences SEQ ID NO: 1 to SEQ ID NO: 6, or an homologous protein thereof.

In a further preferred aspect, the methods according to the invention comprise inhibiting the expression of at least one gene encoding a mitochondrial ribosomal protein using small inhibitory nucleic acids, such as siRNA including shRNA, miRNA. In another aspect, the methods according to the invention comprise inhibiting the expression of at least one gene encoding a mitochondrial ribosomal protein by activation of a transcriptional repressor acting on mitochondrial protein expression or inhibition of transcriptional activators acting on mitochondrial protein expression.

In an alternative preferred aspect, the methods according to the invention comprise administering an antibiotic that targets bacterial translation, such as tetracycline, doxycycline or chloramphenicol.

In a further alternative aspect, the methods according to the invention comprise inhibiting mitochondrial ribosome assembly.

In another embodiment, the invention relates to the use of an agent or composition that induces a nuclear-mitochondrial OXPHOS protein dyssynchrony, in the manufacture of a medicament for increasing lifespan, inhibiting or delaying the aging process; treating, preventing, or delaying, an age-related disease or disorder; and/or treating, preventing, or delaying, a mitochondrial disease or disorder.

In an alternative embodiment, the invention relates to the use of an agent or composition that inhibits the mitochondrial translation machinery function, in the manufacture of a medicament for increasing lifespan, inhibiting or delaying the aging process; treating, preventing, or delaying, an age-related disease or disorder; and/or treating, preventing, or delaying, a mitochondrial disease or disorder.

In a preferred aspect, the invention relates to the use of an agent or composition as described herewith in the manufacture of a medicament for treating, preventing, or delaying, an age-related disease or disorder or a mitochondrial disease or disorder.

More preferably, the invention relates to the use of an agent or composition as described herewith in the manufacture of a medicament for treating, preventing, or delaying, an age-related disease or disorder wherein the medicament is intended for the use in subjects suffering from Parkinson's disease, Alzheimer's disease, obesity, type 2 diabetes, atherosclerosis, reduced kidney function (renal insufficiency), reduced skeletal muscle strength (sarcopenia), chronic inflammatory diseases (arthritis, arthrosis), and anemia, cancers, hearing and vision loss (e.g. age-related macular degeneration and deafness).

Also preferred, is the use of an agent or composition as described herewith in the manufacture of a medicament for treating, preventing, or delaying, a mitochondrial disease or disorder, wherein the medicament is intended for the use in subjects suffering from a mitochondrial disease or disorder selected from Alzheimer's disease, Parkinson's disease, Huntington disease, certain types of blindness and deafness, Leber's hereditary optic neuropathy, Leigh syndrome, mitochondrial myopathies, Neuropathy ataxia retinitis pigmentosa and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), and mtDNA depletion such as mitochondrial neurogastrointestinal encephalomyopathy (MNGIE).

In an alternative embodiment, the invention relates to the use of an antibiotic that targets bacterial translation such as tetracycline, doxycycline or chloramphenicol, in the manufacture of a medicament for increasing lifespan, inhibiting or delaying the aging process, and/or treating, preventing, or delaying, an age-related disease or disorder, and/or treating, preventing, or delaying, a mitochondrial disease or disorder.

In an alternative embodiment, the invention relates to the use of tetracycline in the manufacture of a medicament for increasing lifespan, inhibiting or delaying the aging process, and/or treating, preventing, or delaying, an age-related disease or disorder, and/or treating, preventing, or delaying, a mitochondrial disease or disorder.

In an alternative embodiment, the invention relates to the use of doxycycline in the manufacture of a medicament for increasing lifespan, inhibiting or delaying the aging process, and/or treating, preventing, or delaying, an age-related disease or disorder, and/or treating, preventing, or delaying, a mitochondrial disease or disorder.

In an alternative embodiment, the invention relates to the use of chloramphenicol in the manufacture of a medicament for increasing lifespan, inhibiting or delaying the aging process, and/or treating, preventing, or delaying, an age-related disease or disorder, and/or treating, preventing, or delaying, a mitochondrial disease or disorder.

In a preferred aspect, the invention relates to the use of an antibiotic that targets bacterial translation such as tetracycline, doxycycline or chloramphenicol, in the manufacture of a medicament for treating, preventing, or delaying, an age-related disease or disorder. More preferably, the invention relates to the use of an antibiotic that targets bacterial translation such as tetracycline, doxycycline or chloramphenicol, in the manufacture of a medicament for treating, preventing, or delaying, an age-related disease or disorder, wherein the medicament is intended for the use in subjects suffering from Parkinson's disease, Alzheimer's disease, obesity, type 2 diabetes, atherosclerosis, reduced kidney function (renal insufficiency), reduced skeletal muscle strength (sarcopenia), chronic inflammatory diseases (arthritis, arthrosis), anemia, cancers, hearing and vision loss (e.g. age-related macular degeneration and deafness).

Also preferably, the invention relates to the use of an antibiotic that targets bacterial translation such as tetracycline, doxycycline or chloramphenicol, in the manufacture of a medicament for treating, preventing, or delaying, a mitochondrial disease or disorder wherein the medicament is intended for the use in subjects suffering from a mitochondrial disease or disorder selected from Alzheimer disease, Parkinson disease, Huntington disease, certain types of blindness and deafness, Leber's hereditary optic neuropathy, Leigh syndrome, mitochondrial myopathies, Neuropathy ataxia retinitis pigmentosa and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), and mtDNA depletion such as mitochondrial neurogastrointestinal encephalomyopathy (MNGIE).

A preferred embodiment of the invention relates to the uses of an agent or composition in the manufacture of a medicament as mentioned above, wherein the medicament is intended for inhibiting the mitochondrial translation machinery function mainly in specific tissue(s) and/or organ(s) of a subject. More preferably for inhibiting the expression of at least one gene encoding a mitochondrial ribosomal protein and/or the activity of at least one mitochondrial ribosomal protein, in a subject. Still more preferably, said mitochondrial ribosomal protein is selected among MRPS5, MRPL1 and/or MRPL2, still more preferably said mitochondrial ribosomal protein has any one of the amino acid sequences SEQ ID NO: 1 to SEQ ID NO: 6, or an homologous protein thereof.

In an alternative preferred aspect, the invention relates to the uses of an agent or composition in the manufacture of a medicament as mentioned above, wherein the medicament is intended for inhibiting mitochondrial ribosome assembly in a subject, preferably mainly in specific tissue(s) or organ(s) of said subject.

In a preferred aspect of the methods and uses according to the invention, the specific tissue(s) or organ(s) include liver, muscle, fat, endocrine, or sensory-neural tissues.

Methods of Screening According to the Invention

Another aspect of the invention is a method of screening a compound for its ability to increase lifespan, inhibit or delay the aging process, and/or prevent, treat, or delay an age-related disease or disorder or a mitochondrial disease or disorder, in a subject, comprising:
  a) Contacting a cell or a non-human subject with a test compound; and
  b) Measuring the mitochondrial unfolded protein response ($UPR^{mt}$) in the presence and in the absence of the test compound in said cell or said non-human subject,
wherein a test compound that modulates the $UPR^{mt}$ determined in step b) in the cell or non-human subject indicates a compound that is able to increase lifespan, inhibit or delay the aging process, and/or prevent, treat, or delay an age-related disease or disorder or a mitochondrial disease or disorder.

In a specific aspect of the method of screening according to the invention, a test compound that induces the $UPR^{mt}$ in the cell or non-human subject indicates a compound that is able to increase lifespan, inhibit or delay the aging process, and/or prevent, treat, or delay an age-related disease or disorder or a mitochondrial disease or disorder.

In another aspect of the method of screening according to the invention, a test compound that represses the $UPR^{mt}$ in the cell or non-human subject indicates a compound that is able to increase lifespan, inhibit or delay the aging process, and/or prevent, treat, or delay an age-related disease or disorder or a mitochondrial disease or disorder.

In a specific aspect of the method of screening according to the invention, the mitochondrial unfolded protein response is measured by detecting and determining the activation of the promoter of the gene(s) encoding mitochondrial chaperone(s) such as Heat Shock proteins HSP6, HSP60 in C. elegans, or any homologous protein thereof in another species, or such as the $UPR^{mt}$ protease ClpP (ATP-dependent caseinolytic protease) in C. elegans, or any homologous protein thereof in another species.

A Hsp60 promoter assay can be carried out using human Hsp60 promoter fragment (−603 to +735) that has been amplified and ligated into the pGL3 basic vector (Promega, Madison, Wis., USA) using forward primer 5'-GA-CAACGCGTAACAAAAGAGGGGCGTCAG-3' (SEQ ID NO: 7) and reverse primer 5'-GACACTCGAGCCCT-GAGAAACCAAGTCAGC-3' (SEQ ID NO: 8), and tailing the primers with MluI site (forward) and XhoI site (reverse).

A Clpp promoter assay can be carried out using human Clpp promoter fragment (−1272 to +337) that has been amplified and ligated into the pGL3 basic vector (Promega, Madison, Wis., USA) using forward primer 5'-GACA ACGCGT CTTTCCGGTCTGATCTCCAG-3' (SEQ ID NO: 9) and reverse primer 5'-GACA CTCGAG GTACCGTCTGCTC-CACCAC-3'(SEQ ID NO: 10), and tailing the primers with MluI site (forward) and XhoI site (reverse).

In a preferred embodiment of the method of screening according to the invention, step b) is carried out in transgenic non-human animals comprising the coding sequence of a gene encoding a reporter protein, or part thereof, operably linked to at least one regulatory sequence of a mitochondrial chaperone, such as, for instance, in Hsp-6::GFP and Hsp-60::GFP reporter worms.

In an alternative embodiment of the method of screening according to the invention, step b) is carried out in mammalian cells in culture, for instance, hepatocyte cells (e.g. Hepa 1-6 mouse liver cells, mouse primary hepatocytes), hepatocyte cell lines (e.g. mouse hepatocyte cell line AML-12).

One skilled in the art will understand that any reporter protein can be used in the method of screening according to the invention including fluorescent proteins like Green Fluorescent Protein (GFP) and Red Fluorescent Protein (RFP), luminescent proteins like luciferase, as well as other reporter proteins like β-galactosidase, for instance.

The measurement of fluorescence can be carried out by any standard method including, for instance, fluorescent spectroscopy, fluorescence microscopy, and FACS. The measurement of luminescence can be carried out by any standard method including luminescent spectroscopy, luminescence microscopy.

Another embodiment of the invention is a method of screening a compound for its ability to increase lifespan, inhibit or delay the aging process, and/or prevent, treat, or delay an age-related disease or disorder or a mitochondrial disease or disorder, in a subject, comprising:
a) Contacting a cell or a non-human subject with a test compound; and
b) measuring the ratio between (i) the expression and/or activity of nuclear DNA-encoded OXPHOS proteins and (ii) the expression and/or activity of mitochondrial DNA-encoded OXPHOS proteins in the presence and in the absence of the test compound in said cell or said non-human subject,
wherein a test compound that modulates the ratio of step b) in the cell or non-human subject indicates a compound that is able to increase lifespan, inhibit or delay the aging process, and/or prevent, treat, or delay an age-related disease or disorder or a mitochondrial disease or disorder.

In a specific aspect, a test compound that increases the ratio measured in step b) in the cell or non-human subject indicates a compound that is able to increase lifespan, inhibit or delay the aging process, and/or prevent, treat, or delay an age-related disease or disorder or a mitochondrial disease or disorder.

In an alternative aspect, a test compound that reduces the ratio measured in step b) in the cell or non-human subject indicates a compound that is able to increase lifespan, inhibit or delay the aging process, and/or prevent, treat, or delay an age-related disease or disorder or a mitochondrial disease or disorder.

In a specific embodiment of the invention, the expression of nuclear DNA- and mitochondrial DNA-encoded OXPHOS proteins is measured by detecting the protein production by standard procedures known to the skilled in the art such as Western blot, dot blots, or ELISA.

In another specific embodiment of the invention, the expression of nuclear DNA- and mitochondrial DNA-encoded OXPHOS proteins is measured by determination of the induction of the $UPR^{mt}$ response, which is stimulated by nuclear-mitochondrial OXPHOS protein dyssynchrony, said $UPR^{mt}$ response being measured as described above.

In another specific embodiment of the invention, the activity of nuclear DNA- and mitochondrial DNA-encoded OXPHOS proteins, or the ratio between these two activities, is measured by standard techniques known to the skilled person, including indirect techniques of measuring dyssynchrony such as those for measuring oxygen consumption or respiration. For instance, oxygen consumption can be measured using the Seahorse XF24 equipment (Seahorse Bioscience Inc., North Billerica, Mass.). In particular, the protocol described in Watanabe et al., 2006, Nature 439, 484) can be utilized to measure oxygen consumption in cell culture, and the results can be normalized for protein content. In worms or other non-human animals, oxygen consumption, respiratory exchange ratios, and activity can be monitored by indirect calorimetry using the comprehensive laboratory animal monitoring system (CLAMS) (Columbus Instruments, Columbus, Ohio, USA).

The methods of screening according to the invention can be applied to mammalian cells such as lymphocytes and hematopoietic stem cells, C2C12 myotubes, primary hepatocytes, HepF2 or Hepa1.6 cell lines, or cell lines based on blood-derived cells including, for instance, lymphoblasts. The test compounds can also be tested in animal models (e.g. mice, C. elegans or Drosophila) to evaluate their effect on lifespan.

Test compounds include, for instance, small molecules (such as antibiotics), peptides, peptidomimetics, chimaeric proteins, natural or unnatural proteins, nucleic acid derived polymers (such as DNA and RNA aptamers, siNAs, siRNAs, shRNAs, PNAs, or LNAs), fusion proteins (such as fusion proteins with MRP antagonizing activities), and antibody antagonists (such as neutralizing anti-MRP antibodies).

Test compounds can be selected based on structural or functional similarity to other compounds already known as, for example, inhibiting the bacterial translation machinery or mitochondrial translation machinery in eukaryotes, or are taken from commercially available compound libraries.

The test compound to be used in the screening methods of the invention may be, for instance, polyphenols (e.g. resveratrol, quercetin, fisetin), poly(ADP-ribose)polymerase inhibitors (e.g. PJ-34, hydamtiq, oliparib, iniparib), nicotinamide adenine dinucleotide precursors (e.g. nicotinic acid, nicotinamide, nicotinamide riboside), AMP-activated kinase (AMPK) agonists (e.g. AICAR, metformin, genistein), inhibitors of mTOR (e.g. rapamycin), mitochondrial uncouplers (carbonyl cyanide 4-trifluoromethoxy-phenylhydrazone (FCCP), carbonyl cyanide 3-chlorophenylhydrazone (CCCP), tetrachloro-2-trifluoromethylbenzimidazle), mitochondrial toxins (2,4-Dinitrophenol (DNP), rotenone, arsenic acid, Ethidium Bromide).

Methods of Prognosis or Diagnosis According to the Invention

Another embodiment of the invention relates to an ex-vivo method of prognosis and/or diagnosis of premature aging, or age-related disease or disorder, or mitochondrial disease or disorder, in a patient, comprising:
a) providing a body sample from said patient;
b) measuring the mitochondrial unfolded protein response ($UPR^{mt}$) in said sample;
c) comparing the level of $UPR^{mt}$ determined in step b) with a reference value;
wherein a level of $UPR^{mt}$ determined in step b) that differs from the reference value is indicative of premature aging, development of an age-related disease or disorder, or of a mitochondrial disease or disorder.

In a specific aspect of the ex-vivo method of prognosis and/or diagnosis according to the invention, a level of $UPR^{mt}$ determined in step b) that is lower than the reference value is indicative of premature aging, development of an age-related disease or disorder, or of a mitochondrial disease or disorder.

In another specific aspect of the ex-vivo method of prognosis and/or diagnosis according to the invention, a level of $UPR^{mt}$ determined in step b) that is higher than the reference value is indicative of premature aging, development of an age-related disease or disorder, or of a mitochondrial disease or disorder.

In a specific aspect of the invention, the reference value is the level of $UPR^{mt}$ measured in a body sample from a young patient, and/or a patient without known or suspected age-related disease or mitochondrial disease.

In another specific aspect of the invention, the body sample is selected among serum, plasma, liver, muscle or fat from the patient.

In a specific aspect of the ex-vivo method of prognosis and/or diagnosis according to the invention, the mitochondrial unfolded protein response is measured by detecting and determining the activation of the promoter of the gene(s) encoding mitochondrial chaperone(s) such as HSP6, HSP60 in C. elegans, or any homologous protein thereof in another species such as HSP60 and HSP70 in mammals. The activation of the promoter of the gene(s) encoding mitochondrial chaperone(s) can be detected and determined by any standard method, including determination of the gene expression level of said mitochondrial chaperone(s).

Another embodiment of the invention relates to an ex-vivo method of prognosis and/or diagnosis of premature aging, or age-related disease or disorder, or mitochondrial disease or disorder, in a patient, comprising:
  a) providing a body sample from said patient;
  b) measuring the ratio between (i) the expression and/or activity of nuclear DNA-encoded OXPHOS proteins and (ii) the expression and/or activity of mitochondrial DNA-encoded OXPHOS proteins in said sample;
  c) comparing the ratio determined in step b) with a reference value;
wherein a ratio determined in step b) that differs from the reference value is indicative of premature aging, development of an age-related disease or disorder, or of a mitochondrial disease or disorder.

In a specific aspect of this embodiment of the ex-vivo method of prognosis and/or diagnosis according to the invention, a ratio determined in step b) that is lower than the reference value is indicative of premature aging, development of an age-related disease or disorder, or of a mitochondrial disease or disorder.

In an alternative aspect of this embodiment of the ex-vivo method of prognosis and/or diagnosis, a ratio determined in step b) that is higher than the reference value is indicative of premature aging, development of an age-related disease or disorder, or of a mitochondrial disease or disorder.

In a specific aspect of this embodiment, the reference value corresponds to the ratio between (i) the expression and/or activity of nuclear DNA-encoded OXPHOS proteins and (ii) the expression and/or activity of mitochondrial DNA-encoded OXPHOS proteins measured in a body sample from a young patient, and/or a patient without known or suspected age-related disease or mitochondrial disease.

In another embodiment, the expression of nuclear DNA- and mitochondrial DNA-encoded OXPHOS proteins is measured by detecting the protein production by standard procedures known to the skilled in the art such as Western blot, dot blot, ELISA.

In another specific embodiment of the invention, the expression of nuclear DNA- and mitochondrial DNA-encoded OXPHOS proteins is measured by determination of the induction of the UPR$^{mt}$ response, which is stimulated by nuclear-mitochondrial OXPHOS protein dyssynchrony, said UPR$^{mt}$ response being measured as described above In another specific embodiment of the invention, the activity of nuclear DNA- and mitochondrial DNA- encoded OXPHOS proteins, or the ratio between these activities, is measured by standard techniques known to the skilled person, including indirect techniques of measuring dyssynchrony such as those for measuring oxygen consumption or respiration. For instance, oxygen consumption can be measured using the Seahorse XF24 equipment (Seahorse Bioscience Inc., North Billerica, Mass.). In particular, the protocol described in Watanabe et al., 2006, Nature 439, 484) can be utilized to measure oxygen consumption in cell culture, and the results can be normalized for protein content. In worms or other non-human animals, oxygen consumption, respiratory exchange ratios, and activity can be monitored by indirect calorimetry using the comprehensive laboratory animal monitoring system (CLAMS) (Columbus Instruments, Columbus, Ohio, USA).

Agents and Compositions According the Invention

In another embodiment, the invention relates to an agent or composition that induces a nuclear-mitochondrial OXPHOS protein dyssynchrony for use in increasing lifespan, inhibiting or delaying the aging process, and/or treating, preventing, or delaying, an age-related disease or disorder or a mitochondrial disease or disorder.

In a specific aspect, the agent or composition according to the invention alters the ratio between (i) the expression and/or activity of nuclear DNA-encoded OXPHOS proteins and (ii) the expression and/or activity of mitochondrial DNA-encoded OXPHOS proteins. In a particular aspect of the invention, said ratio is increased.

In a further aspect, the agent or composition according to the invention induces mitochondrial uncoupling.

In a further embodiment, the invention relates to an agent or composition that inhibits the mitochondrial translation machinery function for use in increasing lifespan, inhibiting or delaying the aging process, and/or treating, preventing, or delaying, an age-related disease or disorder or a mitochondrial disease or disorder.

Preferably, the agent or composition according to the invention inhibits the expression of at least one gene encoding a mitochondrial ribosomal protein (MRP) and/or the activity of at least one mitochondrial ribosomal protein (MRP).

Preferably, said MRP is selected among MRPS5, MRPL1 and/or MRPL2, still more preferably the mitochondrial ribosomal protein has any one of the amino acid sequences SEQ ID NO: 1 to SEQ ID NO: 6, or an homologous protein thereof.

In a preferred aspect, the agent or composition according to the invention comprises or consists of an antibiotic that targets bacterial translation, such as tetracycline, doxycycline or chloramphenicol.

In a preferred embodiment, the agent or composition according to the invention is for use in the treatment or prevention of an age-related disease or disorder.

In a specific aspect, the agent or composition according to the invention exerts its inhibitory effect on the mitochondrial translation machinery function in specific tissues or organs of the subject to be treated. Preferably, liver, muscle, fat, endocrine, or sensory-neural tissues.

In another aspect, the invention relates to doxycycline for use in increasing lifespan, inhibiting or delaying the aging process, and/or treating, preventing, or delaying, an age-related disease or disorder or a mitochondrial disease or disorder.

In another aspect, the invention relates to tetracycline for use in increasing lifespan, inhibiting or delaying the aging process, and/or treating, preventing, or delaying, an age-related disease or disorder or a mitochondrial disease or disorder.

In another aspect, the invention relates to chloramphenicol for use in increasing lifespan, inhibiting or delaying the aging process, and/or treating, preventing, or delaying, an age-related disease or disorder or a mitochondrial disease or disorder.

In a further embodiment, the invention provides pharmaceutical compositions and methods for treating a subject, preferably a mammalian subject, and most preferably a human subject who is suffering from an age-related disease or disorder or a mitochondrial disease or disorder, said pharmaceutical composition comprising the agent according to the invention as described herewith.

The agent according to the invention include small molecules (such as antibiotics), peptides, peptidomimetics, chimaeric proteins, natural or unnatural proteins, nucleic acid derived polymers (such as DNA and RNA aptamers, siNAs, siRNAs, shRNAs, PNAs, or LNAs), fusion proteins (such as fusion proteins with MRP antagonizing activities), antibody antagonists (such as neutralizing anti-MRP antibodies), mitochondrial uncouplers.

Pharmaceutical compositions or formulations according to the invention may be administered as a pharmaceutical formulation, which can contain an agent according to the invention in any form.

The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous and intradermal) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Examples of suitable adjuvants include MPL® (Corixa), aluminum-based minerals including aluminum compounds (generically called Alum), ASO1-4, MF59, CalciumPhosphate, Liposomes, Iscom, polyinosinic:polycytidylic acid (polyIC), including its stabilized form poly-ICLC (Hiltonol), CpG oligodeoxynucleotides, Granulocyte-macrophage colony-stimulating factor (GM-CSF), lipopolysaccharide (LPS), Montanide, PLG, Flagellin, QS21, RC529, IC31, Imiquimod, Resiquimod, ISS, and Fibroblast-stimulating lipopeptide (FSL1).

Compositions of the invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions of the invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

The compounds of this invention can also be administered in sustained release forms or from sustained release drug delivery systems.

According to a particular embodiment, compositions according to the invention are for subcutaneous use or oral use.

Alternatively, compositions according to the invention are for intra-ocular delivery, for instance when the patient is suffering from age-related macular degeneration.

In another particular aspect, the compositions according to the invention are adapted for delivery by repeated administration.

Further materials as well as formulation processing techniques and the like are set out in *Part 5 of Remington's Pharmaceutical Sciences*, 21$^{st}$ *Edition*, 2005, Lippincott Williams & Wilkins, which is incorporated herein by reference.

Mode of Administration

Compounds, compositions, and formulations thereof according to this invention may be administered in any manner including orally, parenterally, intravenously, rectally, or combinations thereof. Parenteral administration includes, but is not limited to, intravenous, intra-arterial, intra-peritoneal, subcutaneous, intradermal, intramuscular, and intra-ocular administration. The compositions of this invention may also be administered in the form of an implant, which allows slow release of the compositions as well as a slow controlled i.v. infusion.

Preferentially, the compounds, compositions and formulations thereof according to the invention are administered subcutaneously or orally. Alternatively, the compositions and formulations according to the invention are administered intra-ocularly, for instance when the patient is suffering from age-related macular degeneration.

In one embodiment of the invention, the administration of compounds and compositions of the invention requires multiple successive injections. Thus, the administration can be repeated at least two times, repeatedly or continuously. The period of administration may vary for example from at least 1, 2, 3, or 4 weeks; 2, 3, 4, 5, 6, 8, 10, or 12 months; or 2, 3, 4, or 5 years.

Subjects

Subjects to which the methods and uses according to the invention can be applied are multicellular organisms including animal-models and mammals, preferably including human, primates, laboratory rodents and the like.

In one embodiment, subjects to which a method of treating, preventing, delaying or inhibiting an age-related disease or disorder, or a mitochondrial disease or disorder, according to the invention can be applied are human subjects which may be predisposed to the disease but have not yet been diagnosed as having it. The method of treatment, or use, according to the invention then corresponds to a preventive early asymptomatic intervention. In this case, the method of treatment or use may be applied to the subject prior to the appearance or development of the age-related disease or disorder, preferably a few years before the subject reaches the age at which the age-related disease or disorder usually begins to develop in the subject's species. It is understood that this age also depends on the age-related disease or disorder. Similarly, the method of treatment or use may be applied to the subject prior to the appearance or development of the mitochondrial disease or disorder.

In another embodiment, the methods and uses according to the invention are applied to human subjects who are old and/or afflicted of an age-related disease or disorder.

In another embodiment, the method of screening of compounds according to the invention is applied to animal-models including C. elegans and laboratory rodents such as rat and mice.

Kit

Another object of the invention is a kit for carrying out any one of the methods and uses according to the invention.

In a particular embodiment, the invention relates to a kit of parts for screening a compound for its ability to increase lifespan, inhibit or delay the aging process, and/or prevent, treat, or delay an age-related disease or disorder or a mitochondrial disease or disorder, in a subject, comprising, for example, apparatus, reagents and standard solutions.

Apparatus considered are those developed for carrying out e.g. immunoassays (including ELISAs), fluorimetric assays (for instance a Victor X4 multilabel plate reader (Perkin-Elmer Life Science). Reagents are those reagents particularly developed and designed for the detection and determination of the activation of the promoter of mitochondrial chaperone(s) such as HSP6, HSP60 in C. elegans or any homologous proteins thereof in another species. The kit of parts may contain further hardware, such as pipettes, solutions such as buffers, blocking solutions and the like, filters, color tables and directions for use.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

EXAMPLES

Materials and Methods
Forward Genetics

For the in silico search for longevity genes, publicly available longevity data of the BXD genetic reference population (De Haan and Van Zant, 1999, *FASEB J.* 13, 707) were used. The interval mapping tool of GeneNetwork (www.genenetwork.org) was used to identify a region on chromosome 2, 122-129 Mb, associating with the longevity trait (Trait ID 10112 from BXD Published Phenotypes). Pearson's r genetic correlation of the longevity trait in the BXD eye database (Eye M430v2 Data Set (September 8) RMA) (Geisert et al., 2009, *Mol Vis* 15, 1730) was performed to establish the correlation between longevity and genes in the chromosome 2 region or other genes of interest.

Reverse Genetics

For the reverse genetics approach, a genome correlation analysis for Mrps5 was performed. The eye database of BXD mice (Trait ID 1448488_at from Eye M430v2 (September 8) RMA) and the white adipose tissue database of an F2 cross between C57BL/6J and C3H/HeJ mice, which received a high fat diet from 8-24 weeks of age (Trait ID 10024407239 from UCLA BHF2 Adipose (June 5) mlratio) (Chen et al., 2008, *Nature* 452, 429) were used. Both datasets were analyzed as follows: Mrps5 expression was correlated to genetic traits using a SGO literature correlation method in the respective databases. After sorting the correlated traits for genetic correlation, the top 250 genes were selected, and KEGG and gene ontology analysis were performed following the tools implemented in GeneNetwork. For the network approach, the OXPHOS genes were selected within the top 250 traits associated with Mrps5 and the Pearson correlation coefficients were used to create a network (threshold=0.6). For Ubl5 and Hspd1 correlates, a BXD hippocampus gene expression database (Overall et al., 2009, *Front Neurosci.* 3, 55) was used, as well as adipose tissue data from an F2 intercross (Chen et al., 2008, supra). The Hspd1 network was generated by selecting the OXPHOS and Mrp genes in the top500 correlates in the previously mentioned F2 intercross adipose tissue (threshold=0.75).

Hierarchical Clustering

Unsupervised hierarchical clustering was performed using complete linkage and Pearson rank correlation distance on the normalized metabolites using software implemented in Genepattern (http://www.broadinstitute.org/cancer/software/genepattern/) (Reich et al., 2006, *Nat Genet.* 38, 500; de Hoon et al., 2004, *Bioinformatics* 20, 1453). The z-score was calculated by subtracting the mean expression value for each gene from each of the values and then dividing the resulting values by the standard deviation. Color in the heat-maps reflects the relative gene abundance level with red being higher and blue lower than the mean gene abundance value. Gene ordering is determined as in hierarchical clustering using the distance function 1-correlation.

Cell Culture and Oxygen Consumption

Hepa1-6 mouse liver cells were maintained in DMEM medium containing 4.5 g/l glucose and 10% fetal calf serum. Hepa1-6 cells were incubated for 48 h with doxycycline or chloramphenicol (both Sigma) in medium containing 1 g/l glucose, with 1% (v/v) oleate-BSA (Sigma) supplementation, and without any other antibiotics. Oxygen consumption in Hepa1-6 cells was measured using the Seahorse XF24 equipment (Watanabe et al., 2006, *Nature* 439, 484), and normalized for protein content. ATP content was measured using CellTiter-Glo (Promega), according to the manufacturer's protocol.

Mouse Indirect Calorimetry

Wild type C57BL/6N mice were treated for 10 days with 50 mpkd doxycycline (Sigma) in food admix. Oxygen consumption ($VO_2$), respiratory exchange ratios (RER), and activity were monitored by indirect calorimetry using the comprehensive laboratory animal monitoring system (CLAMS) (Columbus Instruments, Columbus, Ohio, USA).

C. elegans Strains and RNAi Experiments

C. elegans strains were cultured at °° C. on nematode growth media agar plates seeded with E. coli strain OP50 unless stated otherwise. Strains used were wild-type Bristol N2, SJ4100 (zcIs13[hsp-6::GFP]), SJ4058 (zcIs9[hsp-60:: GFP]), SJ4005 (zcIs4[hsp-4::GFP]), SJ4103 (zcIs14[myo-3:: GFP(mit)]), RW1596 stEx30[myo-3p::GFP+rol-6(su1006)], and CL2070 (dvIs[hsp-16.2::GFP]). Strains were provided by the Caenorhabditis Genetics Center (University of Minnesota).

Bacterial feeding RNAi experiments were carried out essentially as described previously (Kamath et al., 2001, *Genome Biol* 2, RESEARCH0002). Clones used were mrps-5 (E02A10.1), mrpl-1 (F33D4.5), mrpl-2 (F56B3.8), cco-1 (F26E4.9) and ubl-5 (F46F11.4). Clones were purchased from GeneService Ltd. Each clone has been sequenced to confirm its identity. Double RNAi experiments were carried out by mixing the bacterial cultures directly before seeding the NGM plates. Controls were RNAi clone 50% diluted with control vector RNAi bacteria.

Worm Lifespan Analysis

Lifespan tests were performed as described (Mouchiroud et al., 2011, *Aging Cell* 10, 39). Briefly, 60-100 animals were used per conditions and scored every other day. All lifespan experiments were performed at 20° C. Animals that crawled off the plate or had an "exploded vulva" phenotype were censored.

Treatments with antibiotics (carbenicillin, doxycycline, and chloramphenicol (all Sigma)) were performed with heat-killed bacteria (Wood et al., 2004, *Nature* 430, 686). Carbenicillin, doxycycline, and chloramphenicol were added at the indicated concentrations. Animals were exposed to antibiotics from eggs to L4 larval stage and then shifted on plates seeded with live OP50 bacteria.

GFP Expression and Quantification

GFP expression and quantification were carried out according to the protocol previously described (Durieux et al, 2011, *Cell* 144, 79). Briefly, GFP was monitored in Day 1 adults. Fluorimetric assays were performed using a Victor X4 multilabel plate reader (Perkin-Elmer Life Science). Eighty roller worms were picked at random (20 worms per well of a black-walled 96-well plate) and each well was read four times and averaged. Each experiment was repeated at least twice.

For picture acquisition, animals were mounted on 2% agarose pads in a droplet of 10 mM tetramisole (Sigma) and examined using a Zeiss Axioplan-2 microscope (Carl Zeiss MicroImaging, Thornwood, N.Y., USA) equipped for both DIC and epifluorescence. Images were obtained using a Coolsnap $ES^2$ camera.

Worm Respiration Assays

Oxygen consumption was measured using the Seahorse XF24 equipment (Seahorse Bioscience Inc., North Billerica, Mass.). Typically, 200 animals per conditions were recovered from NGM plates with M9 medium, washed three times in 2 mL M9 to eliminate residual bacteria, and resuspended in 500 µL M9 medium. Worms were transferred in 24-well standard Seahorse plates (#100777-004) (50 worms per well) and oxygen consumption was measured 6 times. Respiration rates were normalized to the number of worms in each individual well.

Hsp60 Reporter Assays

Human Hsp60 promoter fragment (−603 to +735) was amplified and ligated into the pGL3 basic vector (Promega, Madison, Wis., USA) using forward primer 5'-GACAACGCGTAACAAAAGAGGGGCGTCAG-3' (SEQ ID NO: 7) and reverse primer 5'-GACACTCGAGCCCTGAGAAACCAAGTCAGC-3' (SEQ ID NO: 8). The primers were tailed with MluI site (forward) and XhoI site (reverse).

The mouse hepatocyte cell line AML-12 (alpha mouse liver 12) was obtained from ATCC (Manassas, Va., USA). Cells were grown according to the supplier guidelines but in the absence of antibiotics unless specified.

Transfections were performed in 96-well plates using jet-PEI (PolyPlus transfection, France). Each well contained 30 ng of luciferase reporter and 5 ng of β-galactosidase expression plasmid. After 6 h of incubation with the DNA-jetPEI complexes, the transfection medium was exchanged for medium with or without antibiotic (doxycycline or chloramphenicol). The antibiotic was dissolved in appropriate vehicle (e.g. DMSO (dimethyl sulfoxide) or ethanol) and added to the cells in medium.

Luciferase activity was measured with the luciferase assay system (Promega) in the Victor X4 (PerkinElmer) and normalized to β-galactosidase activity.

Culture of Primary Hepatocytes

Primary hepatocytes were prepared from 8-10 week old C57BL/6 mice by collagenase perfusion method as described in Ryu et al. (2011, *Diabetes*, 60, 1072-1081). Isolated primary hepatocytes were plated with medium 199 (Gibco) including 10% fetal calf serum (FCS), 10 units/ml penicillin and 10 µg/ml streptomycin. After 3-6 h attachment, cells were replaced with media without FCS and treated with 30 µg/ml antibiotic (doxycycline or chloramphenicol) or vehicle for antibiotic dilution every 24 h. Primary hepatocytes were harvested 48 h later.

Western Blotting

Western blotting was performed with antibodies against HSP60 (N-20), HSP90 (BD Transduction Laboratories), β-actin, (Santa Cruz Biotechnology), MitoProfile® Total OXPHOS Rodent WB Antibody Cocktail against, ATP5A (H28016.1 in worms), MTCO1/COX1 (MTCE.26 in worms) and UQCRC2 (Abcam), green fluorescent protein (Cell Signaling) HRP-labeled anti-goat and anti-mouse secondary antibodies.

Statistics

Survival analyses were performed using the Kaplan Meier method and the significance of differences between survival curves calculated using the log rank test. Differences between two groups were assessed using two-tailed t-tests. Analysis of variance, assessed by Bonferroni's multiple comparison test, was used when comparing more than two groups.

The statistical software used was GraphPad Prism 5 (GraphPad Software, Inc.) and all p-values <0.05 were considered significant.

Example 1

Association Between MRP and Lifespan in Mice

The BXD mouse genetic reference population (GRP) constitutes a family of wild-type inbred mice derived from parental C57BL/6J and DBA/2J mice lines, with a level of genetic variation comparable to many human populations. As these lines were inbred, their genotypes were fixed, and as a result phenotypic data can be accumulated to generate massive phenotype data sets. Recently developed genomic and genetic toolsets were used to re-analyze longevity data sets for the BXD GRP (Gelman et al., 1988, *Genetics* 118, 693; De Haan and Van Zant, 1999, supra; Lang et al., 2010, *Aging Clin Exp Res* 22, 8) using both a forward and reverse genetic methods.

Figure 2:
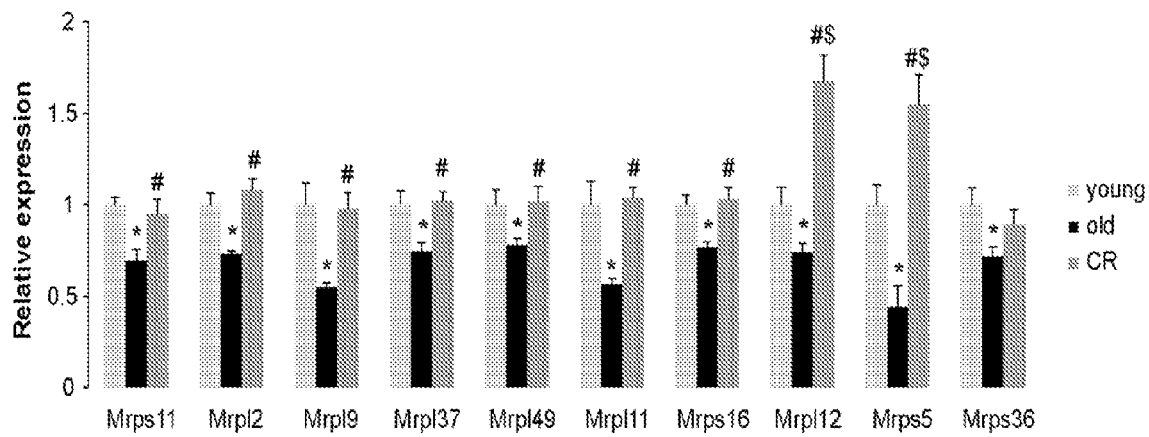
FIG. 2 shows the average values corresponding to the representation of FIG. 1 (C). Black: old, Grey: caloric restricted (CR), Light grey: young, mice.

The forward strategy exploits the longevity data (De Haan and Van Zant, 1999, supra) and new genetic and genomic datasets that are archived in the GeneNetwork web resource. Using updated SNP genotypes, longevity in the BXD family was remapped and a significant locus on chromosome 2 was detected between approximately 122 and 129 Mb. There are 91 known genes in this interval, none of which has been previously linked to longevity. Unlike most other genes in the Quantitative Trait Locus (QTL), the expression of the gene encoding a mitochondrial ribosomal protein, Mrps5, was correlated negatively with lifespan (FIG. 1A). Mrp's involvement in lifespan regulation is strengthened by the fact that several other Mrp family members had significant correlations and associations with longevity (FIG. 1B). Expression of various Mrp genes was checked in a large muscle microarray database of aging and caloric restriction (CR) in the maternal C57BL/6J strain. Interestingly, expression of all Mrp genes that were tested decreased with age, and was reverted by CR (FIGS. 1C and 2). The analyses were extended to the DNA level using online sequence data for Mrps5 in both parental strains and extracted a comprehensive list of sequence variants. In the case of Mrps5 there are two missense variants in exon 3 (rs29667217 and rs13471334; V60A and V67I, respectively). Additional variants in Mrps5 modulate expression, and genetic variation in the expression of this gene is associated with a strong QTL that is superimposed over the gene itself (a so-called cis-QTL). Expression of Mrps5 is also modulated by at least two distant or trans-QTLs.

To establish how well Mrps5 is associated with longevity, the network membership of this gene was studied in two large and independent expression data sets using a reverse genetics approach. Mrps5 was tightly linked with a set of genes involved in oxidative phosphorylation (OXPHOS) across the BXD family. Considering that oxidative metabolism is an important downstream effect of known longevity pathways, including the AMPK and sirtuin pathways, this Mrps5 covariate gene set qualified as an appealing longevity network. Detailed KEGG pathway analysis confirmed that OXPHOS was the most significantly correlated pathway with Mrps5 (p=1.53e-21). White adipose tissue has already proven to be powerful in longevity studies (Argmann et al., 2009, *PLoS Genet.* 5(12): e1000752; Bluher et al., 2003, *Science* 299, 572). Therefore, this analysis was extended using adipose tissue data sets from an F2 intercross, in which Mrps5 was linked to an electron transport network (p=5.78e-10). Finally, an interaction network of OXPHOS genes with Mrps5 was generated (data not shown), in which Ndufb7 provided the hinge that links Mrps5 to OXPHOS. Mrps5 is clearly an interesting longevity gene that appears to integrate protein synthesis and mitochondrial metabolism, both of which are important factors modulating longevity.

Example 2

Figure 3:
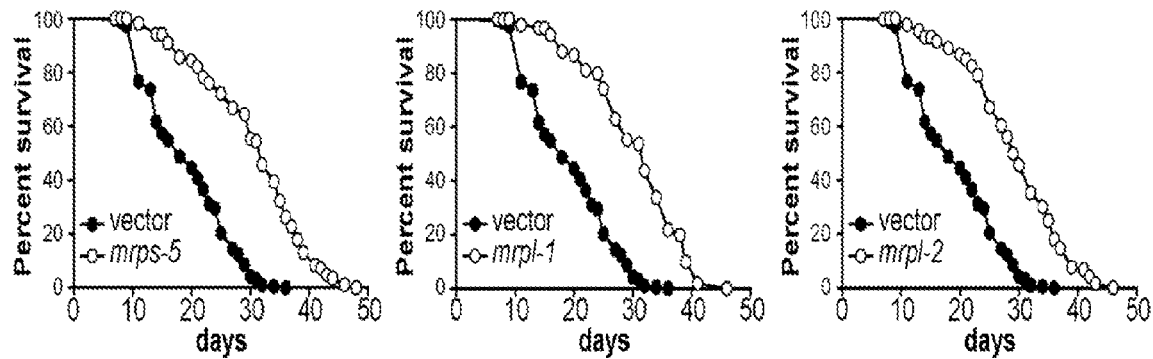
FIG. 3 shows the link between mitochondrial ribosomal proteins and metabolic lifespan regulation in *C. elegans*. (A) Knockdown of mrps-5, mrpl-1 or mrpl-2 genes in *C. elegans* increased lifespan by 60%, 57% or 54%, respectively, compared to empty vector treated worms (p<0.001; n=2-4 individual experiments). (B) Knockdown of MRP genes in *C. elegans* decreased respiration as evaluated by Seahorse respirometry. ***p≤0.001.
Figure 3:
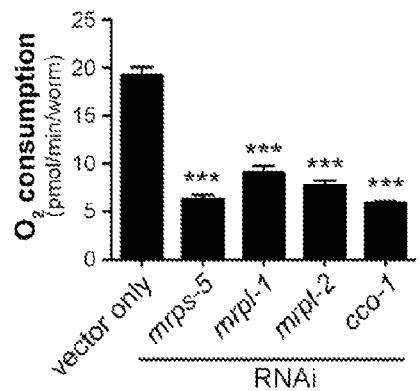

Association Between MRPs and Longevity in *C. elegans* and Effects of Mrps Knock-Down Because of the association between the Mrp's and mouse lifespan, the power of *C. elegans* genetics was exploited to define potential causality of these Mrp's in determining longevity. Using BLAST search, the E02A10.1, F33D4.5, and F56B3.8 genes were identified as worm homologs for Mrps5, Mrpl1, and Mrpl2, respectively. These genes were knocked down during the entire life of the worm, resulting in a ~60% increase in lifespan (FIG. 3A). The knockdown during development proved crucial, as RNAi during adulthood alone did not affect lifespan (data not shown). The assessment of the morphological changes upon aging in the worm muscle using the $p_{myo-3}$MYO-3::GFP reporter showed a remarkable delay in muscle fiber disorganization in worms treated with mrps-5 RNAi (data not shown).

As many nutrient networks implied in longevity impact mitochondrial respiration (Lee et al., 2010, *Curr Biol* 20, 2131), respiration was analyzed using live worms after two days of adulthood. Upon Mrp knockdown respiration was robustly reduced (FIG. 3B), an effect accompanied by a change in mitochondrial morphology, showing a more punctuate pattern instead of the regular reticular appearance (data not shown). Increased lifespan was not due to effects on feeding behavior, as pharyngeal pumping rates were not affected. Aged mrps-5 RNAi worms at day 13 move approximately twice as much as controls, and this effect becomes more pronounced at day 20. This physiological difference was accompanied by a delay in the decline of pharyngeal pumping and in muscle fiber disorganization, hallmarks of improved fitness of aging mrps-5 RNAi worms.

Example 3

MRP Genes Confer Longevity Effects Through Mitochondrial Unfolded Protein Response To further clarify the mechanism that is triggered by Mrp inactivation, stress responses, in particular the mitochondrial unfolded protein response ($UPR^{mt}$), were investigated.

Figure 4:
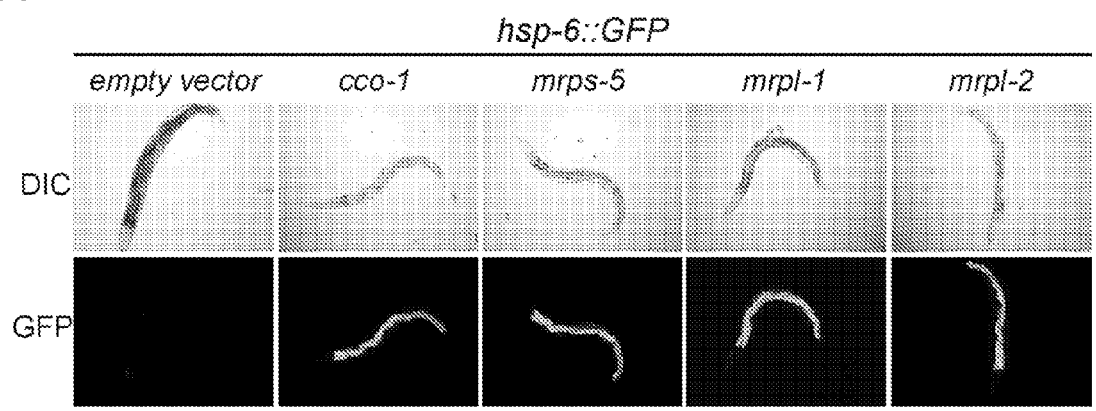
FIGS. 4 to 6 show that MRP genes confer longevity effects through mitochondrial unfolded protein response.
Figure 4:
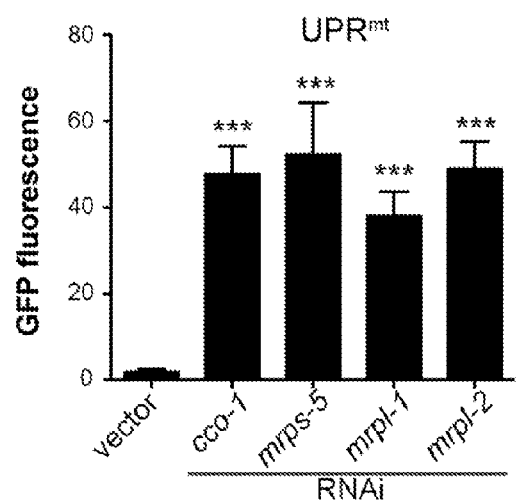
Figure 4:
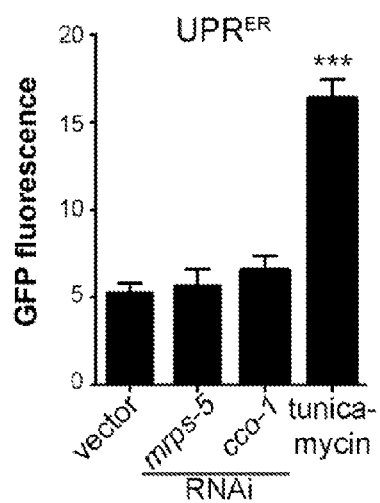

The activity of the $UPR^{mt}$ was measured using hsp-6::GFP and hsp-60::GFP reporter worms with reduced mrp expression. Similar to the mitochondrial OXPHOS mutant cco-1 (Durieux et al., 2011, supra), hsp-6 and hsp-60 were induced (indicative for $UPR^{mt}$ activation) in worms with reduced mrps-5, mrpl-1, or mrpl-2 expression (FIG. 4A-B). The stress response was specific for $UPR^{mt}$, as both unfolded protein response in the ER ($UPR^{ER}$), as measured in the hsp-4::GFP reporter strain, and cytosolic heat shock response, evaluated using the hsp-16.2::GFP reporter, were not affected following mrps-5 knockdown (FIG. 4C). As for lifespan, the $UPR^{mt}$ was not induced in worms in which mrp expression was only inhibited during adulthood (data not shown).

Individual differences in the degree of $UPR^{mt}$ were observed within the mrps-5 RNAi worm population. The level of $UPR^{mt}$ correlated tightly with lifespan extension, with high expressers having the longest lifespan (~44 days), worms with no $UPR^{mt}$ showing control lifespan (~22 days), and weak expressers showing an intermediate phenotype (~35 days). Importantly, GFP expression stayed similar throughout life, demonstrating that the effect is not an artifact of a transient reduction in food intake. To further validate the link between the level of $UPR^{mt}$ and lifespan extension, $UPR^{mt}$ activation was measured in worms in which a series of previously identified mrp genes were inactivated. Reduced expression of each mrp gene tested activated $UPR^{mt}$, although to a different degree. Strikingly, the level of $UPR^{mt}$ again correlated significantly with lifespan extension.

Figure 5:
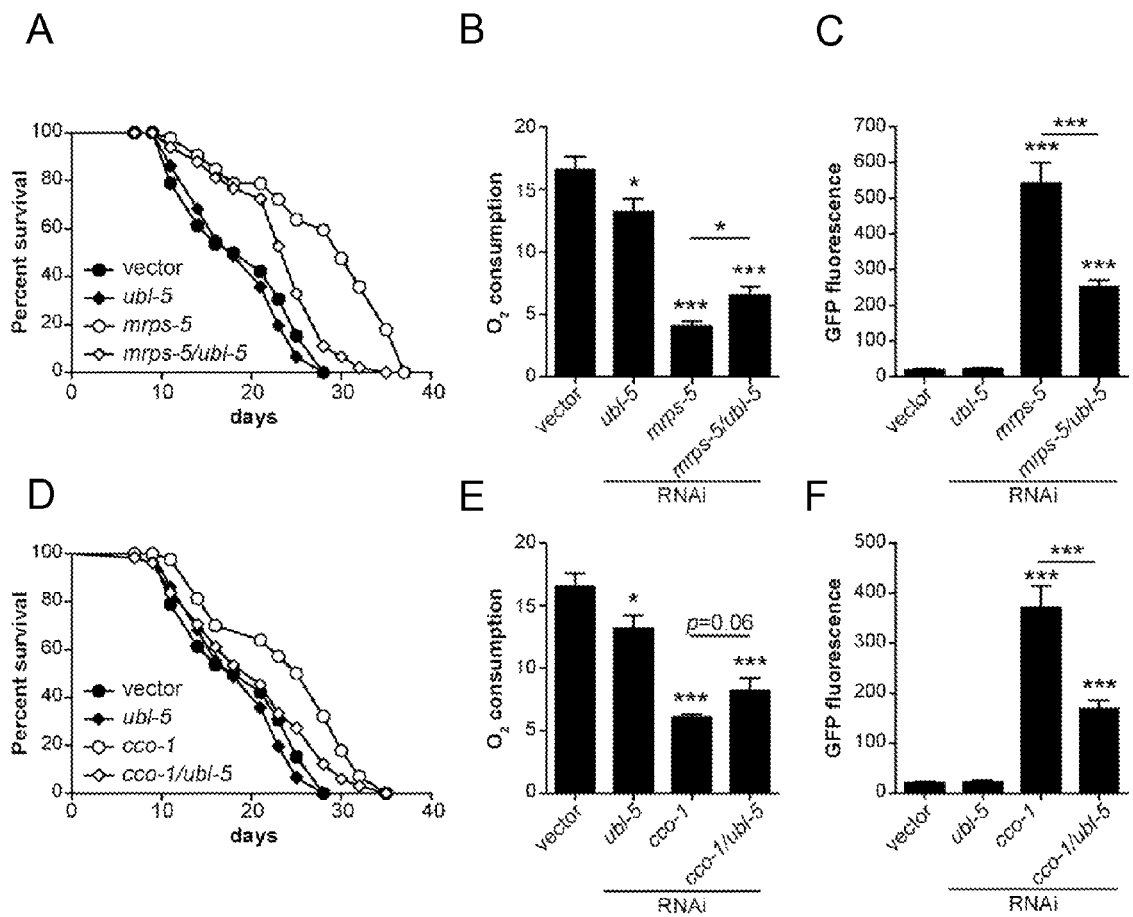

A common downstream effector of $UPR^{mt}$ is UBL5, a ubiquitin-like protein that associates with the homeobox-containing transcription factor DVE1 and thereby facilitates expression of mitochondrial chaperones during $UPR^{mt}$. Indeed, when both ubl-5 and mrps-5 were knocked down, the lifespan extension was partially lost, as well as the oxygen consumption phenotype and $UPR^{mt}$ response (FIG. 5A-C). Importantly, these data were fully in line with data of double knockdown of cco-1 and ubl-5, which, also shows a partial restoration of these parameters (FIG. 5D-F).

Figure 6:
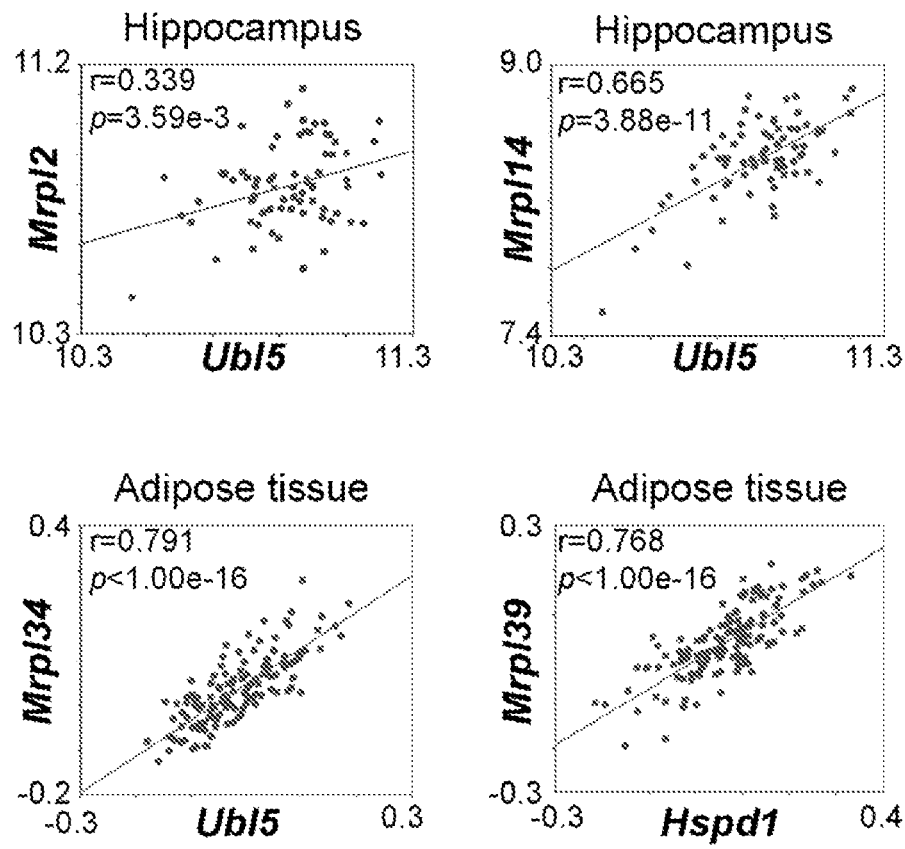

Interestingly, this network could be traced back to mice, as Ubl5 expression correlates with that of several Mrp genes, for instance in hippocampus of the BXD strains and in adipose tissue of F2 intercrossed mice (FIG. 6). Additionally, Hspd1 (the gene encoding mouse HSP-60) correlated robustly with multiple Mrp genes (FIG. 6). Gene ontology analysis revealed a strong connectivity between Ubl5 and OXPHOS genes (p=9e-4 in eye; p=8.62e-10 in hippocampus), Ubl5 and the translation process or ribosome (p=6e-4 in eye;

p=6.03e-10 in hippocampus), and Ubl5 and mitochondrial inner membrane (p=1 e-4 in eye; p=3.31e-27 in hippocampus) in the BXD family. Finally, Hspd1 was tied in a close correlation network with various Mrp genes and genes involved in OXPHOS (data not shown).

Example 4

Figure 7:
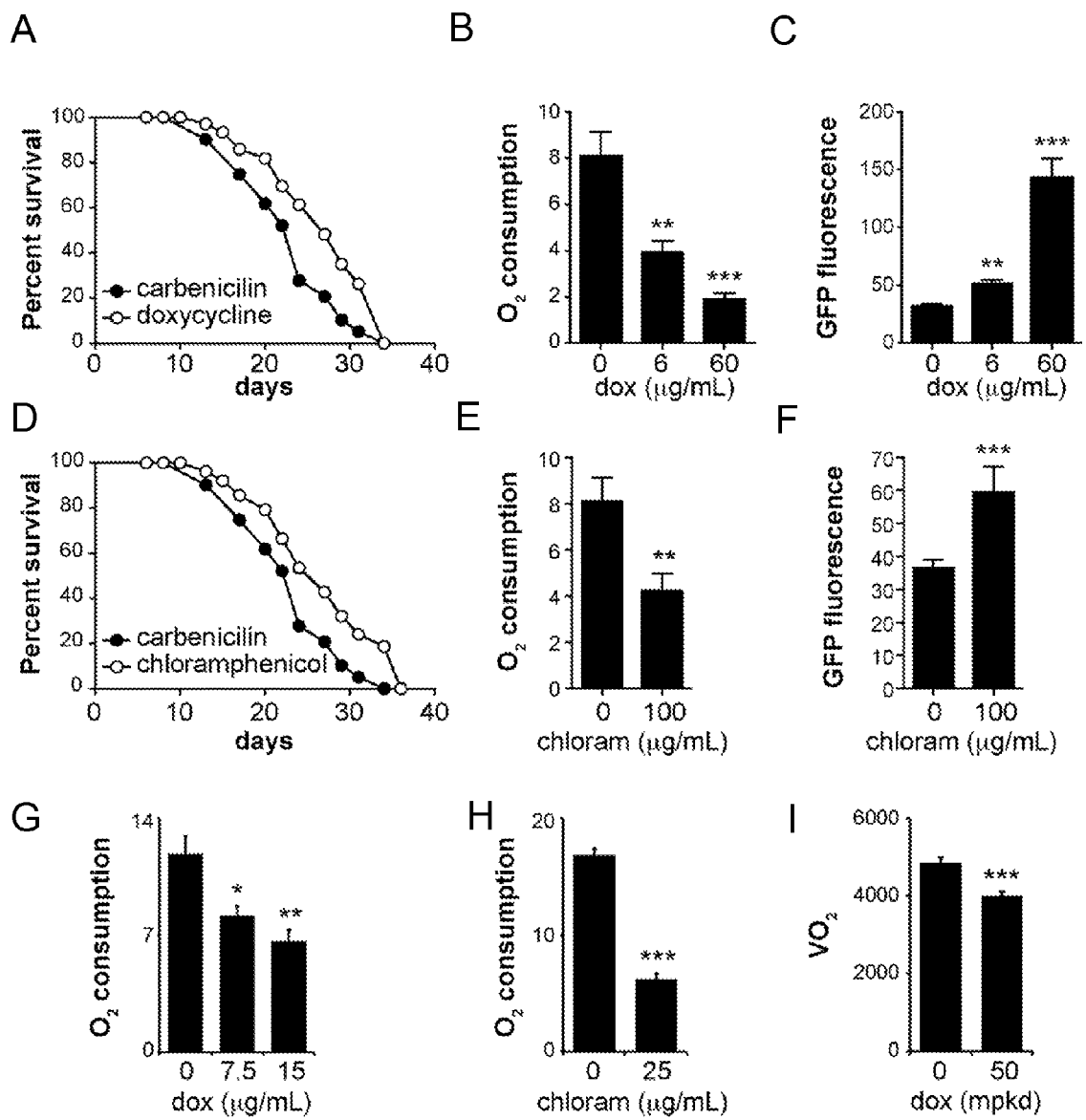
FIG. 7 shows the effects of antibiotics in worms' and mice's longevity. Doxycycline (A-C) and chloramphenicol (D-F) extend lifespan of *C. elegans* (A, D), reduced oxygen consumption (B, E) and induced $UPR^{mt}$ (C, F). Mouse Hepa1-6 liver cells showed decreased respiration following treatment with doxycycline (G) or chloramphenicol (H). (I) Mice treated with 50 mpkd doxycycline for 10 days displayed decreased oxygen consumption. *p≤0.05; p≤0.01; *p≤0.001. Abbreviations are: dox for doxycycline, chloram for chloramphenicol.
Figure 8:
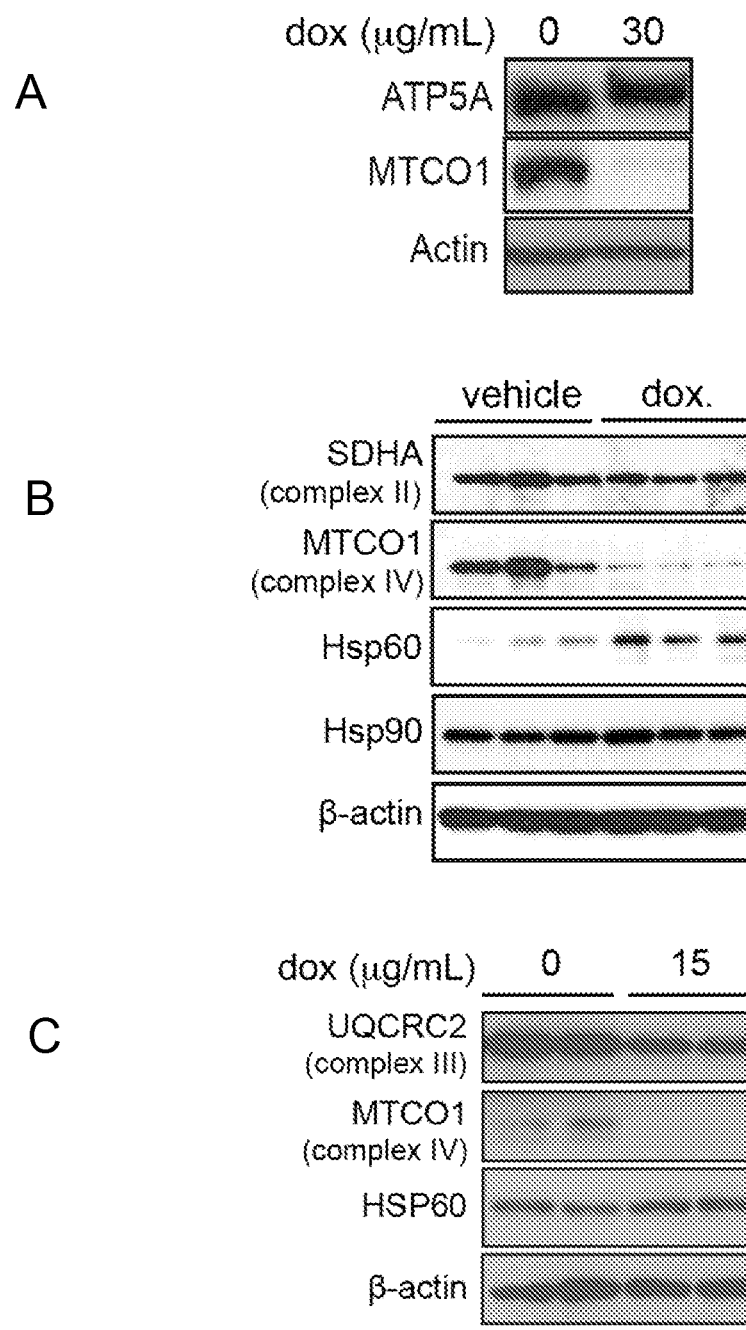
FIG. 8 shows the conserved function of OXPHOS dyssynchrony and $UPR^{mt}$ in ongevity Doxycycline alters the ratio between nDNA-(ATPSA) and mtDNA-(MTCO1) encoded OXPHOS proteins in worms (A), increased HSP60 protein expression and altered the ratio of nDNA-(SDHA) versus mtDNA-(MTCO1) encoded proteins in primary murine hepatocytes (B), increased HSP60 protein expression and altered the ratio of nDNA-(UQCRC2) versus mtDNA-(MTCO1) encoded proteins in a cultured hepatocyte cell line (C). Abbreviations are: dox for doxycycline, nDNA for nuclear DNA, mtDNA for mitochondrial DNA.

Effects of Inhibiting the Mitochondrial Translation Machinery by Antibiotics in *C. elegans* and Mice The mitochondrial translation machinery is involved in translation of the 13 mitochondrial-encoded subunits of oxidative phosphorylation complexes, and is highly conserved throughout evolution, consistent with the hypothesis of endosymbiosis. Antibiotic classes that are known to target bacterial translation, such as tetracyclines, also inhibit eukaryotic mitochondrial translation. Therefore, the tetracycline and doxycycline were used to confirm the involvement of mitochondrial translation in longevity. Carbenicillin, a penicillin-type antibiotic that targets the bacterial cell wall, was used as a control. Treatment of *C. elegans* with doxycycline extended lifespan (FIG. 7A), with a concurrent reduction in oxygen consumption (FIG. 7B). $UPR^{mt}$ was also dose-dependently induced by doxycycline (FIG. 7C), to a level similar as observed by mrps-5 RNAi, without activation of $UPR^{ER}$ (data not shown). Supporting that these effects are dependent on mitochondrial translation per se, and not specific for doxycycline, is the fact that chloramphenicol, belonging to a different class of antibiotics that target bacterial translation, also extended lifespan (FIG. 7D), decreased respiration (FIG. 7E), and induced $UPR^{mt}$ (FIG. 7F). Similar to mrps-5 RNAi, doxycycline increased the ratio of nDNA-(ATP5A) over mtDNA-encoded (MTCO1) OXPHOS proteins in *C. elegans* (FIG. 8A).

Finally, these results were translated back to mammals by treating the mouse Hepa1-6 liver cell line with doxycycline. Similar to worms, doxycycline decreased respiration in Hepa1-6 cells, suggestive for reduced mitochondrial activity (FIG. 7G), without affecting cell viability as measured by ATP levels (data not shown). Again, chloramphenicol confirmed that the effects on oxygen consumption in mammalian cells were not doxycycline-specific (FIG. 7H). Finally, in C57BL/6 mice, fed for 10 days with chow containing doxycycline, oxygen consumption was significantly reduced during the light cycle (FIG. 7I) without changes in body weight, food intake or activity (data not shown), testifying of decreased resting energy expenditure. Doxycycline also increased HSP60 protein expression, both in hepatocyte cell lines (FIG. 8C) and in primary murine hepatocytes (FIG. 8B). Like in worms, also in these two hepatocyte models, doxycycline not only induced UPRmt, but also resulted in a striking OXPHOS protein dyssynchrony (FIG. 8B,C). Finally, feeding mice with doxycycline for 10 days lowered their oxygen consumption, indicative for attenuated mitochondrial function in vivo.

In summary, these data implicate MRPs as an evolutionary conserved longevity protein family. It is shown, here, that the role of mitochondrial translation in longevity is conserved from *C. elegans* to mammals. Importantly, the murine data indicate that expression of Mrps5, Mrpl1, and Mrpl12 contribute to natural lifespan regulation, probably by enhanced stress defense involving the $UPR^{mt}$. These data also generally support the role of MRPs in longevity via the induction of a nDNA-/mtDNA-encoded OXPHOS dyssynchrony leading to activation of the mitochondrial unfolded protein response ($UPR^{mt}$).

```
                          List of sequences

Human MRPS5 (P82675)
                                                              SEQ ID NO: 1
    1 matavravgc lpvlcsgtag hllgrqcsln tlpaasilaw ksvlgnghls slgtrdthpy
   61 aslsralqtq ccisspshlm sqqyrpysff tkltadelwk galaetgaga kkgrgkrtkk
  121 kkrkdlnrgq iigegrygfl wpglnvplmk ngavqtiaqr skeegekvea dmiggreewd
  181 rkkkmkvkre rgwsgnswgg islgppdpgp cgetyedfdt rilevrnvft mtakegrkks
  241 irvlvavgng kgaagfsigk atdrmdafrk aknravhhlh yieryedhti fhdislrfkr
  301 thikmkkmok gyglrchrai iticrligik dmyakvsgsi nmlsltqglf rglsrgethq
  361 gladkkglhv veireecgpl pivvasprgp lrkdpepede vpdvkldwed vktaggmkrs
  421 vwsnlkraat Human MRPL1 (Q9BYD6)
                                                              SEQ ID NO: 2
    1 maaavrcmgr alihhqrhsl skmvyqtslc scsvnirvpn rhfaaatksa kktkkgakek
   61 tpdekkdeie kikaypymeg epeddvylkr lyprqiyeve kavhllkkfq ildftspkqs
  121 vyldltldma lgkkknvepf tsvlslpypf aseinkvavf tenasevkia eengaafagg
  181 tsliqkiwdd eivadfyvav peimpelnrl rkklnkkypk lsrnsigrdi pkmlelfkng
  241 heikvdeere nflqtkiatl dmssdqiaan lqavinevcr hrplnlgpfv vraflrssts
  301 eglllkidpl lpkevknees ekeda Human MRPL2 (Q5T653)
                                                              SEQ ID NO: 3
    1 malcaltral rslnlapptv aapapslfpa aqmmnngllq gpsalmllpc rpvltsvaln
   61 anfvswksrt kytitpvkmr ksggrdhtgr irvhgigggh kgryrmidfl rfrpeetksg
  121 pfeekviqvr ydpersadia lvaggsrkrw iiatenmgag dtilnsnhig rmavaaregd
  181 ahplgalpvg tlinnvesep grgagyiraa gtcgvllrkv ngtaiiqlps krqmqvletc
  241 vatvgrvsnv dhnkrvigka grnrwlgkrp nsgrwhrkgg wagrkirplp pmksyvklps
  301 asaqs Mouse MRPS5 (Q99N87) Mus musculus
                                                              SEQ ID NO: 4
    1 maaavraagc lpalcslqag hflsrqlsln afpvaatsfl avktalshgs lssretrrnh
   61 cltslshvlq tqccvsspgn wtgqqcrpys fftkltaeel wkgalaetga garkgrgkrt
  121 kkkkrkdlnr gqiigegrsg flwpglnvpl iksgvvqnig qrskeeqqkv eatmveciree
  181 wdrkrkikvk rergwsgntw ggvsigppdp gpngetyedf dtrilevrnv fnmtakegrk
  241 ksvrvlvavg ngngaagfai gkaadrgdaf rkaknraihy lhyieryegh tifhdislrf
  301 krtgirmkkg prgyglrchr aiiticrlig ikdmyarvtg smnmlnitrg lfhglarciet
```

```
                              List of sequences
361 hqhladkkgl hvvefreecg plpivvasph galskepepe pevpdtkldw qdvkamqglk
421 rsvwfnlkrp at Mouse MRPL1 (Q99N96) Mus musculus
                                                              SEQ ID NO: 5
  1 maaavrclrr vlihhqrhcl ckmasqasly pcsvnsllhn rhfaaaaaaa tkparkikkg
 61 akektsdekp vddiekiksy tymesdpedd vylkrlyprr iyevekaihl lkkfqvldft
121 npkqgvyldl tldmalgkkk tvepfasvia lphlfssevn kvavftanas eikiaeenga
181 afaggtdlvk kimddevvvd fyvavpeimg elnplrkklk krfpkatrns igrdipkmle
241 lfktaheimv deerqnflst kiatldmpsd qiaanlqavi nevckhrpin lgpfvvrafl
301 rsstseglll ktdsllpkea ktteaeteet qtaeaa Mouse MRPL2 (Q9D773) Mus musculus
                                                              SEQ ID NO: 6
  1 malcaltsal rslslasaai tarvptllpa aqiqsnvllq lppalvspsy rpvhmsadrs
 61 akfvswksrt kytvkpvkmr ksggrdhtgr irvhgigggh kqnyrmidfl rfrpekekap
121 epfeekvvvv rydpcrsadi alvaggsrkr wiiatenmka gdtilnsnhi grmavaaqeg
181 dahplgalpv gtlinnvese pgrgaqyira agtcgvllrk vngtaiiqlp skrqmqvles
241 ctatvgrvsn vnhnqrvigk agrnrwlgkr pnsglwqrkg gwagrkirpl ppmksyvklp
301 saaaqn Forward primer for human Hsp60 promoter amplification
                                                              SEQ ID NO: 7
gacaacgcgt aacaaaagag gggcgtcag Reverse primer for human Hsp60 promoter amplification:
                                                              SEQ ID NO: 8
gacactcgag ccctgagaaa ccaagtcagc Forward primer for human Clpp promoter amplification
                                                              SEQ ID NO: 9
gacaacgcgt ctttccggtc tgatctccag Forward primer for human Clpp promoter amplification
                                                              SEQ ID NO: 10
gacactcgag gtaccgtctg ctccaccac
```

---

The invention claimed is:

1. A method of increasing lifespan in a subject, the method comprising inducing nuclear-mitochondrial OXPHOS protein dyssynchrony in said subject by inhibiting the mitochondrial translation machinery function by inhibiting the expression of at least one gene encoding a mitochondrial ribosomal protein with a small inhibitory nucleic acid targeting the mRNA of said at least one gene, in said subject, wherein said at least one mitochondrial ribosomal protein is MRPS5, MRPL1 and/or MRPL2.

2. A method of inhibiting or delaying the aging process in a subject, the method comprising inducing nuclear-mitochondrial OXPHOS protein dyssynchrony in said subject by inhibiting the mitochondrial translation machinery function by inhibiting the expression of at least one gene encoding a mitochondrial ribosomal protein with a small inhibitory nucleic acid targeting the mRNA of said at least one gene, in said subject, wherein said at least one mitochondrial ribosomal protein is MRPS5, MRPL1 and/or MRPL2.

3. A method of treating, or delaying, an age-related disease or disorder or a mitochondrial disease or disorder, in a subject, the method comprising administering to said subject in need thereof an effective amount of an agent or composition that induces a nuclear-mitochondrial OXPHOS protein dyssynchrony in said subject by inhibiting the mitochondrial translation machinery function by inhibiting the expression of at least one gene encoding a mitochondrial ribosomal protein with a small inhibitory nucleic acid targeting the mRNA of said at least one gene, in said subject, wherein said at least one mitochondrial ribosomal protein is MRPS5, MRPL1 and/or MRPL2.

4. The method according to claim 3, wherein said disease or disorder is selected from Parkinson's disease, Alzheimer's disease, obesity, type 2 diabetes, atherosclerosis, reduced kidney function, reduced skeletal muscle strength (sarcopenia), chronic inflammatory diseases, anemia, cancers, hearing and vision loss, Huntington disease, Leber's hereditary optic neuropathy, Leigh syndrome, mitochondrial myopathies, Neuropathy ataxia retinitis pigmentosa and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), and mtDNA depletion.

5. The method according to claim 1, wherein said method comprises inhibiting the expression of the gene encoding the mitochondrial ribosomal protein MRPS5 in said subject.

6. The method according to claim 1, comprising administering to said subject a small interfering RNA targeting the mRNA of said mitochondrial ribosomal protein.

7. The method according to claim 2, wherein said method comprises inhibiting the expression of the gene encoding the mitochondrial ribosomal protein MRPS5 in said subject.

8. The method according to claim 2, comprising administering to said subject a small interfering RNA targeting the mRNA of said mitochondrial ribosomal protein.

9. The method according to claim 3, wherein said method comprises inhibiting the expression of the gene encoding the mitochondrial ribosomal protein MRPS5 in said subject.

10. The method according to claim 3, comprising administering to said subject a small interfering RNA targeting the mRNA of said mitochondrial ribosomal protein.

11. The method according to claim 1, wherein said method comprises inhibiting the expression of at least the gene encoding the mitochondrial ribosomal protein MRPL1, in said subject.

12. The method according to claim 2, wherein said method comprises inhibiting the expression of at least the gene encoding the mitochondrial ribosomal protein MRPL1, in said subject.

13. The method according to claim 3, wherein said method comprises inhibiting the expression of at least the gene encoding the mitochondrial ribosomal protein MRPL1, in said subject.

14. The method according to claim 1, wherein said method comprises inhibiting the expression of at least the gene encoding the mitochondrial ribosomal protein MRPL2, in said subject.

15. The method according to claim 2, wherein said method comprises inhibiting the expression of at least the gene encoding the mitochondrial ribosomal protein MRPL2, in said subject.

16. The method according to claim 3, wherein said method comprises inhibiting the expression of at least the gene encoding the mitochondrial ribosomal protein MRPL2, in said subject.

17. The method according to claim 3, wherein said disease or disorder is selected from Parkinson's disease, Alzheimer's disease, obesity, type 2 diabetes, cancers, hearing and vision loss, Huntington disease, Leber's hereditary optic neuropathy, Leigh syndrome, mitochondrial myopathies, Neuropathy ataxia retinitis pigmentosa and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), and mtDNA depletion.

\* \* \* \* \*